US007479385B2

(12) United States Patent
Thorson

(10) Patent No.: US 7,479,385 B2
(45) Date of Patent: Jan. 20, 2009

(54) SUGAR KINASES WITH EXPANDED SUBSTRATE SPECIFICITY AND THEIR USE

(75) Inventor: Jon S. Thorson, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 459 days.

(21) Appl. No.: 10/904,941

(22) Filed: Dec. 6, 2004

(65) Prior Publication Data
US 2005/0208633 A1    Sep. 22, 2005

Related U.S. Application Data

(60) Provisional application No. 60/481,742, filed on Dec. 5, 2003.

(51) Int. Cl.
*C12N 9/12* (2006.01)
(52) U.S. Cl. ..................................................... 435/194
(58) Field of Classification Search ........................ None
See application file for complete search history.

(56) References Cited

FOREIGN PATENT DOCUMENTS

| WO | WO 02/48331 A2 | 6/2002 |
| WO | WO 02/48331 A3 | 6/2002 |
| WO | WO 02/079150 A2 | 10/2002 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Weymouth-Wilson, A.C. (1997) Nat. Prod. Rep. 14, 99-110.
Potier, P. (1999) Actual. Chim. 11, 9-11.
Kren, V., & Martinkova, L. (2001) Curr. Med. Chem. 8, 1303-1328.
Thorson, J.S., et al. (2001) Curr. Org. Chem. 5, 139-167.
Albermann, C., et al (2003) Org. Lett. 5, 933-936.
Mendez, C., Trends in Biotechnology, vol. 19, No. 11, 449-456.
Barton, W.A., et al (2002) Proc. Natl. Acad. Sci. USA99, 13397-13402.
Barton, W.A., et al (2001) Nat. Struct. Biol. 8, 545-551.
Thorson, J.S., et al (2003) ChemBioChem, 5:16-25.
Jiang, J., et al (2003) ChemBioChem.4, 443-446.
Fu, X., et al. (2003) Nat. Biotech. 21: 1467-1469.
Jiang, J., et al. (2001) Angew. Chem. Intl. Ed. 40 1502-1505.
Jiang, J., et al. (2000) J. Am. Chem. Soc. 122, 6803-6804.
Johnson, L.N., & Barford, D. (1990) J. Biol. Chem. 265, 2409-2412.
Park, S. H., et al. (1998) J. Biol. Chem. 273, 5685-5691.
Lavine, J.E., et al. (1982) Biochim. Biophys. Acta 717, 76-85.
Dey, P.M. (1983) Eur. J. Biochem: 136, 155-159.
Thomas, P., et al. (1974) Biochem. J. 139, 661-664.
Yang, J., et al. (2003) Org. Lett. 5, 2223-2226.
Bornscheuer, U.T., & Pohl, M. (2001) Curr. Opin. Chem. Biol. 5, 137-143.
Petrounia, I. P., & Arnold, F. H. (2000) Curr. Opin. Biotechnol. 11, 325-330.
Tao, H., & Cornish, V. W. (2002) Curr. Opin. Chem. Biol. 6, 858-864.
Williams, G. J., et al. (2003) Proc. Natl. Acad. Sci. USA100, 3143-3148.
Wada, M., et al. (2003) Bioorg. Med. Chem. 11, 2091-2098.
DeSantis, G., et al. (2003) Bioorg. Med. Chem. 11, 43-52.
Leung, D.W., et al. (1989) Technique 1, 11-15.
Cadwell, R.G., & Joyce, G. F. (1992) PCR Meth. Appl. 2, 28-33.
Liebeton, K., et al. (2000) Chem. Biol. 7, 709-718.
Stemmer, W.P.C. (1994) Nature 370, 389-391.
Zhao, H., et al. (1998) Nat. Biotech. 16, 258-261.
Kikuchi, M., et al., (1999) Gene 236, 159-167.
Coco, W.M., et al., (2001) Nat. Biotech. 19, 354-359.
Miyazaki, K. (2002) Nuc. Acids Res. 30, e139.
Zha, D., et al., (2003) ChemBiochem 4, 34-39.
Thoden, J.B., & Holden, H. M. (2003) J. Biol. Chem. 278 33305-33311.
Debouck, C., et al., (1985) Nuc. Acids Res. 13, 1841-1853.
Paulsen, H., et al., (1967) Chem. Ber. 100, 2822-2836.
Paulsen, H., & Herold, C. P. (1970) Chem. Ber. 103, 2450-2462.
Bradford, M. (1976) Anal. Biochem. 72, 248-254.
Fromant, M., et al., (1995) Analyt. Biochem. 224, 347-353.
Bork, P., et al., (1993) Protein Sci. 2, 31-40.
Aleshin, et al., (1998) Structure 6, 39-50.
Segura, M.J.R., et al. (2002) Org. Lett. 4, 4459-4462.
Joubert, B. M., et al. (2000) Org. Lett. 2, 339-341.
Herrera, J. B., et al. (2000) J. Am. Chem. Soc. 122, 6765-6766.
Segura, M. J., et al. (2003) Nat. Prod. Rep. 20, 304-317.
Otten, L. G., et al. (2002) J. Biol. Chem. 277, 42121-42127.
Hoffmeister, D., et al. (2003) Proc. Natl. Acad. Sci. USA 100, 13184-13189.
Hoffmeister, D., & Thorson, J. S. (2004) ChemBioChem 5, 989-992.
Yang, J., et al. (2004) ChemBioChem 5, 992-996.
Northrup, A. B. & MacMillan, D. W. (2004) Science. 305, 1752-1755.
Northrup, A.B. et al., (2004) Angew Chem Int Ed Engl. 43, 2152-2154.
Yang, J., et al., (2004) Bioorg. Med. Chem. 12, 1577-1584.
Langenhan, J. M., & Thorson, J. S. (2005) Curr. Org. Syn. 2, 59-8.
Zhang, J., et al. (2003) Org. Biomol. Chem. 1, 3048-3053.

(Continued)

*Primary Examiner*—Sheridan Swope
(74) *Attorney, Agent, or Firm*—Quarles & Brady LLP

(57) ABSTRACT

One preferred embodiment of the present invention provides a GalK variant comprising a Y371H, M173L or Y371H-M173L mutation for in vivo and in vitro glycorandomization. In another preferred embodiment, the *E. coli* GalK variant is mutated at one or more amino acids including R28, E34, D37, D174, Y233, C339, Y371, Y371H, M173, M173L and C353. The GalK variants display catalytic activity toward a variety of D or L sugars. Another preferred embodiment provides method of phosphorylating sugars comprising the step of incubating a nucleotide triphosphate (NTP) and a D or L sugar in the presence of a GalK variant such that a sugar phosphate is produced. This sugar phosphate may be further incubated with a nucleotidylyltransferase, such that a NDP-sugar is produced. The NDP-sugar may be further incubated with a biomolecule capable of being glycosylated in the presence of a glycosyltransferase, such that a glycosylated biomolecule is produced.

5 Claims, 11 Drawing Sheets

OTHER PUBLICATIONS

Zhang, J., et al., (2003) Methods Enzymol. 362, 106-124.
Luchansky, S. J. et al., (2003) Methods Enzymol. 362, 249-272.
Fuster, M. M. et al., (2003) Cancer Res. 63, 2775-2781.
Mong, T. K. et al., (2003) Chembiochem. 4, 835-840.
Shao, Jr., et al., (2003) Appl. Environ. Microbiol. 69, 5238.5342.

* cited by examiner $^3J_{H-H}$ coupling constant

NOESY correlations

FIGURE 9
a)
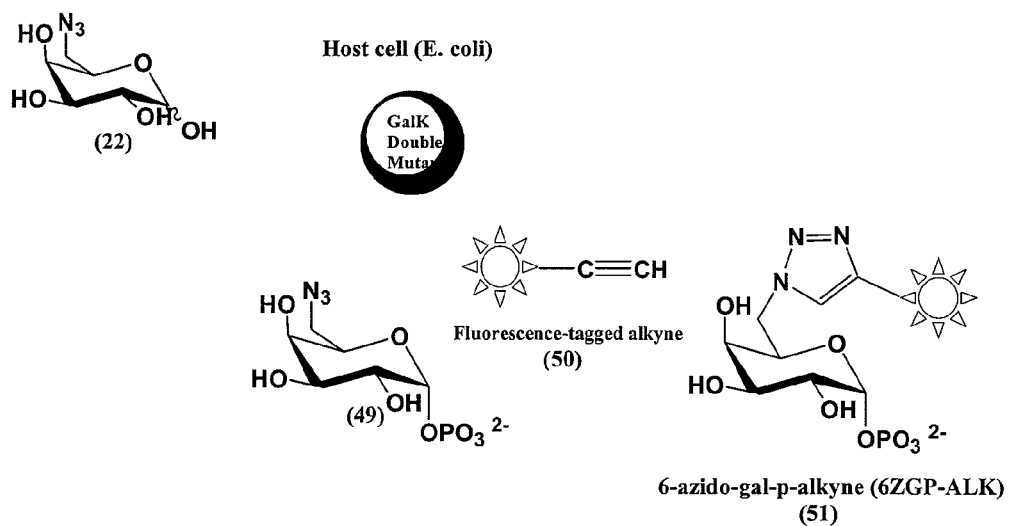
b)
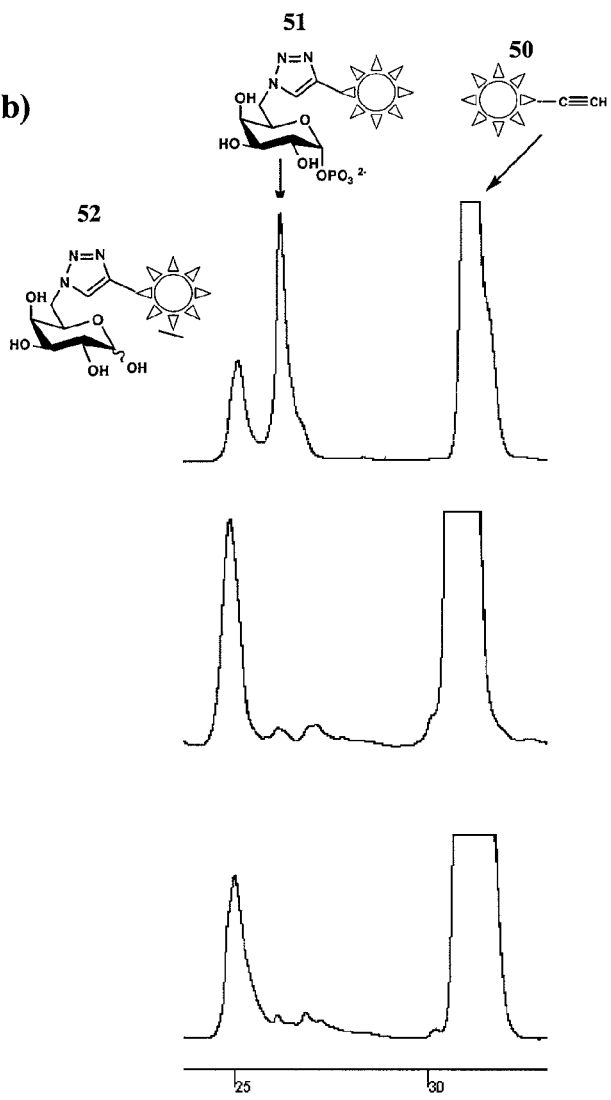

SUGAR KINASES WITH EXPANDED SUBSTRATE SPECIFICITY AND THEIR USE

CROSS-REFERENCE TO RELATED APPLICATIONS

The present application claims the benefit of U.S. Provisional 60/481,742, filed Dec. 5, 2003, which is incorporated by reference herein to the extent that it is not inconsistent with the present disclosure.

STATEMENT REGARDING FEDERALLY-SPONSORED RESEARCH AND DEVELOPMENT

The present invention was supported in part by contribution from the National Institutes of Health grant AI52218. The government of the United States of America may have certain rights in this invention.

BACKGROUND OF INVENTION

This invention generally relates to sugar kinases and specifically to novel anomeric D/L sugar kinases with expanded substrate specificity and methods of use.

Many clinically important medicines are derived from glycosylated natural products, the D- or L-sugar substituents of which often dictate their overall biological activity. This paradigm is found throughout the anticancer and antiinfective arenas with representative clinical examples (FIG. 1a) including enediynes (calicheamicin, 1), polyketides (doxorubicin, 2; erythromycin, 3), indolocarbazoles (staurosporine, 4), non-ribosomal peptides (vancomycin, 5), polyenes (nystatin, 6), coumarins (novobiocin, 7), or cardiac glycosides (digitoxin, 8). Given the importance of the sugars attached to these and other biologically significant metabolites, extensive effort has been directed in recent years toward altering sugars as a means to enhance or alter natural product-based therapeutics by both in vivo and in vitro approaches. Among these, in vitro glycorandomization (IVG) makes use of the inherent or engineered substrate promiscuity of nucleotidylyltransferases and glycosyltransferases to activate and attach chemically synthesized sugar precursors to various natural product scaffolds. This efficiently incorporates highly functionalized "unnatural" sugar substitutions into the corresponding natural product scaffold (FIG. 1b).

Accordingly, the need remains for natural and/or engineered enzymes that are promiscuous in their substrate specificity and capable of increased catalytic activity to enhance multiplicity of available glycosylated natural compounds.

SUMMARY OF INVENTION

The present invention provides sugar kinases with expanded subtrate specificity and methods of use. One embodiment of the present invention provides a GalK variant for in vivo glycorandomization selected from the group consisting of a Y371H, M173L and Y371H-M173L mutation. The GalK variant displays substrate specificity toward a D or L sugar. Preferably, the D or L sugar may be selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

Another embodiment of the present invention provides a method of providing a sugar phosphate. The method comprises the step of incubating a nucleotide triphosphate (NTP) and a D or L sugar in the presence of a GalK variant according to claim 1, such that a sugar phosphate is produced. In this method, the NTP is ATP. Also this method may be carried out in a host cell. Further, in this method, the D or L sugar includes galactose or glucose-configured sugars having substitutions at C-2, C-3, C-4, C-6 positions. Preferably, the D or L sugar include D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

Yet another embodiment of the present invention provides an E. coli GalK variant mutated at one or more amino acid residues. The mutations are selected from the group consisting of R28, E34, D37, D174, Y233, C339, Y371, Y371H, M173, M173L and C353. This variant is capable of displaying catalytic activity toward a D or L sugar selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose. In a preferred embodiment, the GalK variant is Y371H-M173L.

Another embodiment of the present invention provides a method of phosphorylating sugars. This method comprises the step of incubating a nucleotide triphosphate (NTP) and a D or L sugar in the presence of a GalK variant according as discussed above, such that a sugar phosphate is produced. In this method also, the NTP is ATP. Further, the method is carried out in a host cell. Also the D or L sugar in this method is selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

Yet another aspect of the present invention provides a method of synthesizing an NDP-sugar. This method comprises the steps of: (a) incubating a nucleotide triphosphate (NTP) and a D or L sugar in the presence of a GalK variant as discussed, whereby a sugar phosphate is produced; and (b) incubating the sugar phosphate with a nucleotidylyltransferase, such that a NDP-sugar is produced. In this method, the D or L sugar is selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose. Further, the nucleotidylyltransferase is Ep or a mutated variant thereof. Preferably, the mutated Ep variant includes an Ep mutated at one or more amino acids selected from the group consisting of V173, G147, W224, N112, G175, D111, E162, T201, I200, E199, R195, L89, L89T, L109, Y146 and Y177. In this method also, the NTP is ATP. Also in this method the GalK variant is Y371H, M173L or Y371H-M173L. This method may be carried out in vitro or in a host cell. When the method is carried out in a host cell, the host cell is preferably a bacterium. More preferably, the host cell is selected from the group consisting of E. coli and S. lividans.

Another aspect of the invention provides a method of producing a glycosylated biomolecule containing at least one sugar moeity. The method comprises the steps of: (a) incubating a nucleotide triphosphate (NTP) and a D or L sugar in the presence of a GalK variant such that a sugar phosphate is produced; (b) incubating the sugar phosphate with a nucleotidylyltransferase, such that a NDP-sugar is produced; and (c) incubating the NDP-sugar with a biomolecule capable of being glycosylated in the presence of a glycosyltransferase, whereby a glycosylated biomolecule is produced. Preferably in this method, the D or L sugar is selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose. Also, preferably, the nucleotidylyltransferase is Ep or a mutated variant thereof. Mutated Ep variant includes Ep that is mutated at one or more amino acids selected from the group consisting of V173, G147, W224, N112, G175, D111, E162, T201, I200, E199, R195, L89, L89T, L109, Y146 and Y177. Further the glycosyltransferase is selected from the group consisting of CalB, CalE, CalN, CalU, Gra orfl4, Gra orf5, LanGT1, LanGT2, LanGT3, LanGT4, MtmGI, MtmGII, MtmGTIII, MtmGTIV, NovM, RhlB, Rif orf 7, SnogD, SnogE, SnogZ, UrdGT1a, UrdGT1b, UrdGT1c, UrdGT2, AknK, AknS, DesVI, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof. Also in this method, the NTP is ATP. Preferably, the GalK variant is Y371H, M173L or Y371H-M173L. This method may be carried out in vitro or in a host cell. When the method is carried out in a host cell, preferably, the host cell is a bacterium. More preferably, the host cell is selected from the group consisting of *E. coli* and *S. lividans*. Also, in this method the biomolecule capable of being glycosylated is selected from the group consisting of natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, hybrids consisting of one or more these components, analogs and bioactive aglycons thereof. Furthermore, the glycosylated biomolecule is further incubated with at least one chemoselectively ligatable moiety, such that at least one chemoselectively ligated compound is produced.

Various other features, objects, and advantages of the invention will be apparent to those skilled in the art from the following detailed description including illustrative examples setting forth how to make and use the invention.

BRIEF DESCRIPTION OF DRAWINGS

FIG. 9. In vivo GalK-catalyzed sugar-1-phosphate production. (a) Experimental overview using 6-azido-6-deoxy-D-galactose (22) as an example: 22 is fed to an *E. coli* host expressing the M173L-Y371H GalK double mutant and the reactants and products subsequently labeled using a 1,3-dicycloaddition with the fluorescent tag 50. (b) HPLC chromatographs of bioconversions: i)$_{22}$ with Y371H-M173L GalK; ii)$_{46}$ with Y371H-M173L GalK; iii) 22 with wild-type GalK. MS: 50, calculated for $C_{20}H_{25}N_3O_3S$ 387.2, found m/z 386.1 [M−H]$^-$; 51, calculated for $C_{26}H_{37}N_6O_{11}PS$ 672.2, found m/z 671.2 [M−H]$^-$; 52, calculated for $C_{26}H_{36}N_6O_8S$ 592.2, found m/z 591.2 [M−H]

DETAILED DESCRIPTION

Figure 2:
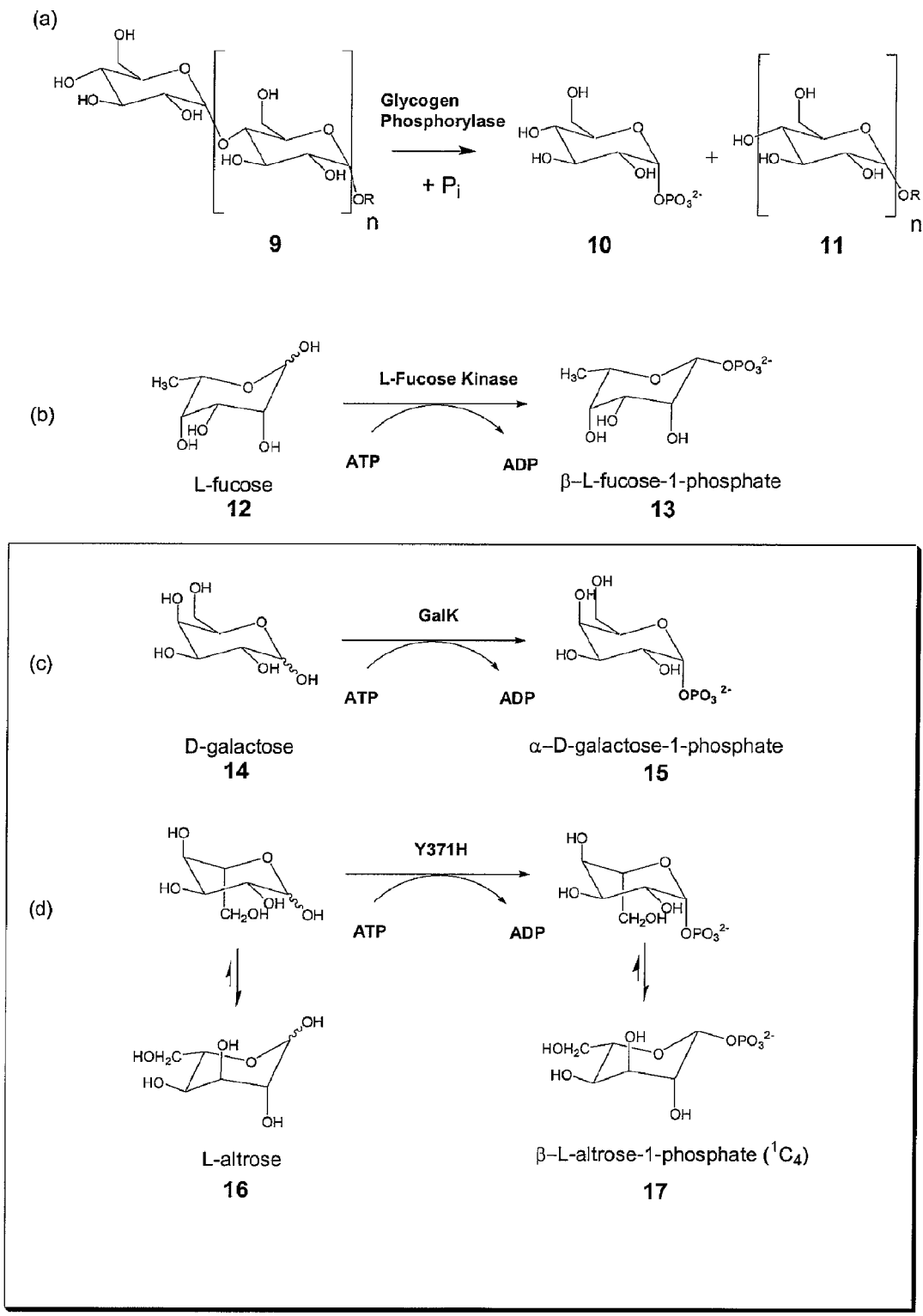
FIG. 2. Provides reactions catalyzed by anomeric kinases. a) Glycogen phosphorylase. b) Fucokinase. c) Galactokinase. d) Proposed phosphorylation of L-altrose accomplished by the evolved GalK mutant Y371H.

Sugar phosphates, as the starting material, play a key role in the entire IVG process. Thus, the ability to rapidly construct sugar phosphate libraries would directly contribute to the efficiency of IVG. Compared with the existing chemical synthetic methods for anomeric phosphorylation, single step enzymatic (kinase) routes bypass required multistep synthetic manipulations and could be coupled to IVG in a single reaction vessel. Known C-1 phosphorylating enzymes are limited to mainly three types (FIG. 2): the glycogen phosphorylases which convert glycogen (9) into D-glucose-1-phosphate (10), fucokinases which transfer a phosphate from ATP to the anomeric position of L-fucose (12) to provide β-L-fucose-1-phosphate (13), and the galactokinases (GalK), which catalyze the formation of α-D-galactose-1-phosphate (Gal-1-P, 15) from D-galactose (14) and ATP. Previous studies have revealed GalK from various sources have a limited substrate scope and in all C-1 kinases studied thus far, a strict adherence to either D-sugars (GalK and glycogen phosphorylases), or L-sugars (as in fucokinase) was observed. Thus, in order to apply any of these kinases for generating a randomized sugar phosphate library, their monosaccharide substrate promiscuity must first be enhanced.

Figure 1:
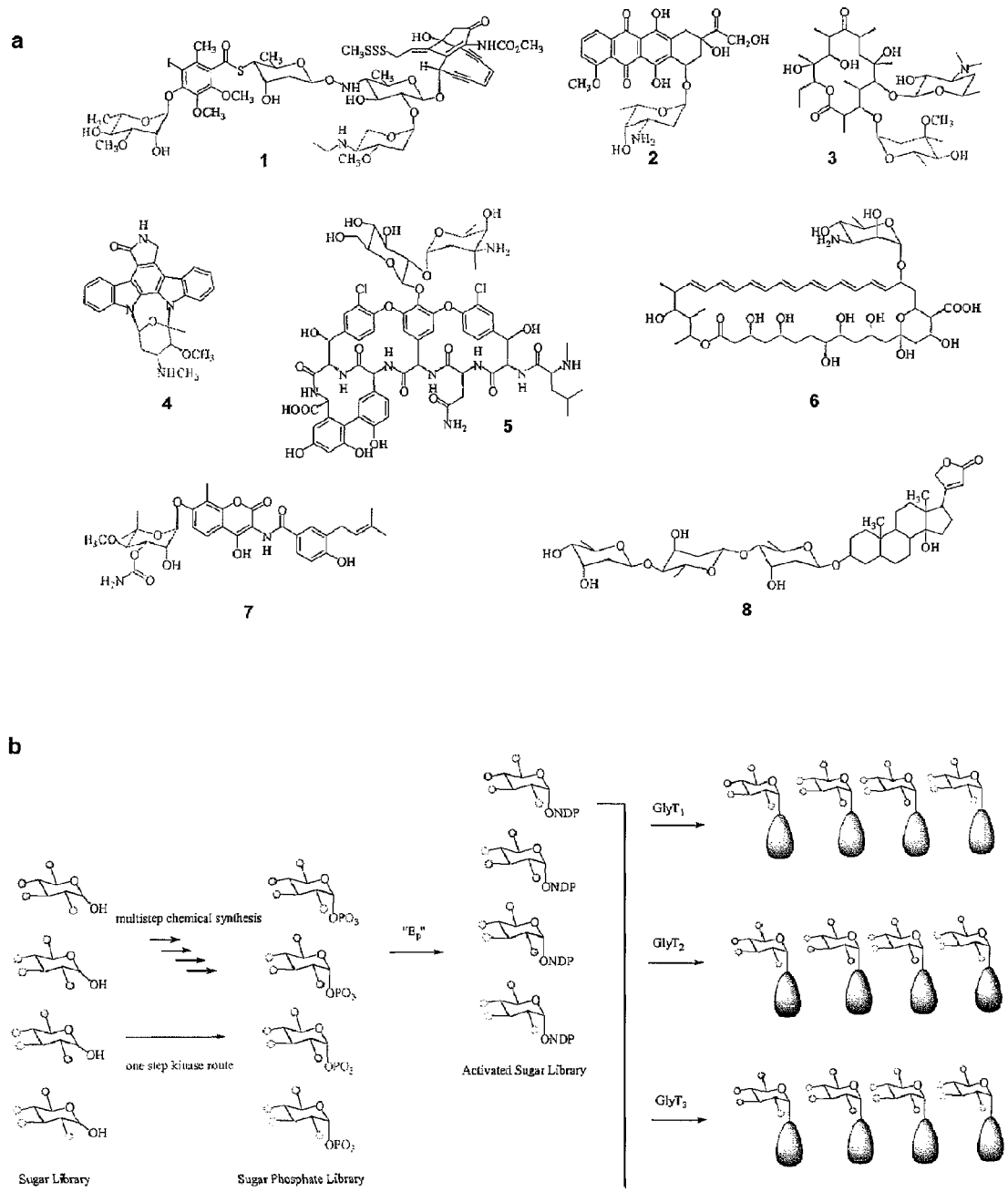
FIG. 1. *a*) Provides representative examples for natural product glycosides used as therapeutics: calicheamicin (1), doxorubicin (2), erythromycin (3), staurosporine (4), vancomycin (5), nystatin (6), novobiocin (7), and digitoxin (8). The attached sugars are highlighted in color with red indicating L-configured sugars, and blue representing D-sugars. b) Schematic for natural product in vitro glycorandomization. $E_p$ denotes αt-D-glucopyranosyl phosphate thymidylyltransferase, $GlyT_n$ different glycosyltransferases.

Two general routes for altering enzyme substrate specificity are currently available. Structure-based engineering relies upon knowledge of an enzyme's three dimensional structure and an explicit molecular-level understanding of substrate recognition. An example of structure-based engineering as applied to IVG includes increasing the substrate scope of nucleotidylyltransferases employed (FIG. 1b, "Ep"). The application of Ep rational engineering led to active site mutants capable of accepting a variety of substrates not utilized by the wild-type enzyme. Such techniques are also described in the U.S. Patent Publications 2003/0055235A1 and 2003/0068669A1, and International Publications WO02079150 and WO0248331, which are incorporated herein by reference in their entirety for all purposes.

The alternative to rational engineering is enzyme evolution, a process primarily dependent upon the availability of a selection or high throughput screen for the desired enhanced or altered enzymatic properties. With respect to carbohydrate enzymology, recent applications include the tagatose-1,6-bisphosphate aldolase modified by in vitro evolution toward an unnatural stereoselectivity, an evolved N-acetylneuraminic acid aldolase for L-sialic acid synthesis, or a 2-deoxy-D-ribose-5-phosphate aldolase with an expanded substrate range after site directed mutagenesis. Usually, in vitro evolution strategies include error-prone PCR for gene diversification, and/or locating critical amino acid residues for saturation mutagenesis or, more prominently, shuffling of fragmented diversified genes or gene families according to a number of different protocols. Subsequently, the diversified proteins are subjected to a screen. In a recent demonstration of IVG, >50 analogs of 5 (vancomycin) were generated, some of which displayed enhanced and distinct antibacterial profiles from the parent natural product.

While the first structure for a sugar C-1 kinase (GalK from *Lactococcus lactis*) recently emerged, the extreme variability in solution structures among anticipated monosaccharide library members and the availability of a specific high throughput sugar anomeric kinase calorimetric screen prompted an initial evolutionary approach. As a model system, the inventors selected the well-characterized *Escherichia* (*E.*) *coli* galactokinase GalK and focused the evolutionary approach toward significant C-5 (e.g. L-sugar variants) and C-6 alterations (e.g. deoxy, amino, uronic acid derivatives) in an attempt to probe and elucidate the specific enzymatic architecture responsible for restricting substrate substitution at C-5 and C-6. All variants used herein to describe sugar kinases are defined as unnaturally occurring variants of naturally occurring sugar kinases.

Herein the inventors describe the application of directed evolution and a high throughput multi-sugar calorimetric screen to enhance the catalytic capabilities of the *E. coli* Gal K. From this approach, one particular GalK mutant carrying a single amino acid exchange (Y371H) displayed a surprisingly substantial degree of kinase activity toward sugars as diverse as D-galacturonic acid, D-talose, L-altrose, and L-glucose, all of which failed as wild-type GalK substrates. Furthermore, this mutant provides enhanced turnover of the small pool of sugars converted by the wild-type enzyme. Comparison of this mutation to the recently solved structure of *Lactococcus* lactis GalK, begins to provide a blueprint for further engineering of this vital class of enzyme. In addition, the rapid access to such promiscuous sugar C-1 kinases will significantly enhance accessibility to natural and unnatural sugar-1-phosphates and thereby impact upon both in vitro and in vivo glycosylation methodologies such as natural product glycorandomization.

Generally the present invention provides sugar kinases with expanded subtrate specificity and methods of use. One embodiment of the present invention provides a GalK variant for in vivo glycorandomization selected from the group consisting of a Y371H, M173L and Y371H-M173L mutation. The GalK variant displays substrate specificity toward a D or L sugar. Preferably, the D or L sugar may be selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

Another embodiment of the present invention provides a method of providing a sugar phosphate. The method comprises the step of incubating a nucleotide triphosphate (NTP) and a D or L sugar in the presence of a GalK variant according to claim 1, such that a sugar phosphate is produced. In this method, the NTP is ATP. Also this method may be carried out in a host cell. Further, in this method, the D or L sugar includes galactose or glucose-configured sugars having substitutions at C-2, C-3, C-4, C-6 positions. Preferably, the D or L sugar include D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

Yet another embodiment of the present invention provides an *E. coli* GalK variant mutated at one or more amino acid residues. The mutations are selected from the group consisting of R28, E34, D37, D174, Y233, C339, Y371, Y371H, M173, M173L and C353. This variant is capable of displaying catalytic activity toward a D or L sugar selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose. In a preferred embodiment, the GalK variant is Y371H— M173L.

Another embodiment of the present invention provides a method of phosphorylating sugars. This method comprises the step of incubating a nucleotide triphosphate (NTP) and a D or L sugar in the presence of a GalK variant according as discussed above, such that a sugar phosphate is produced. In this method also, the NTP is ATP. Further, the method is carried out in a host cell. Also the D or L sugar in this method is selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

Yet another aspect of the present invention provides a method of synthesizing an NDP-sugar. This method comprises the steps of: (a) incubating a nucleotide triphosphate (NTP) and a D or L sugar in the presence of a GalK variant as discussed, whereby a sugar phosphate is produced; and (b) incubating the sugar phosphate with a nucleotidylyltransferase, such that a NDP-sugar is produced. In this method, the D or L sugar is selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose. Further, the nucleotidylyltransferase is Ep or a mutated variant thereof. Preferably, the mutated Ep variant includes an Ep mutated at one or more amino acids selected from the group consisting of V173, G147, W224, N112, G175, D111, E162, T201, I200, E199, R195, L89, L89T, L109, Y146 and Y177. In this method also, the NTP is ATP. Also in this method the GalK variant is Y371H, M173L or Y371H-M173L. This method may be carried out in vitro or in a host cell. When the method is carried out in a host cell, the host cell is preferably a bacterium. More preferably, the host cell is selected from the group consisting of *E. coli* and *S. lividans*.

Another aspect of the invention provides a method of producing a glycosylated biomolecule containing at least one sugar moiety. The method comprises the steps of: (a) incubating a nucleotide triphosphate (NTP) and a D or L sugar in the presence of a GalK variant such that a sugar phosphate is produced; (b) incubating the sugar phosphate with a nucleotidylyltransferase, such that a NDP-sugar is produced; and (c) incubating the NDP-sugar with a biomolecule capable of being glycosylated in the presence of a glycosyltransferase, whereby a glycosylated biomolecule is produced. Preferably in this method, the D or L sugar is selected from the group consisting of D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose. Also, preferably, the nucleotidylyltransferase is Ep or a mutated variant thereof. Mutated Ep variant includes Ep that is mutated at one or more amino acids selected from the group consisting of V173, G147, W224, N112, G175, D111, E162, T201, I200, E199, R195, L89, L89T, L109, Y146 and Y177. Further the glycosyltransferase is selected from the group consisting of CalB, CalE, CalN, CalU, Gra orf14, Gra orf5, LanGT1, LanGT2, LanGT3, LanGT4, MtmGI, MtmGII, MtmGTIII, MtmGTIV, NovM, RhlB, Rif orf7, SnogD, SnogE, SnogZ, UrdGT1a, UrdGT1b, UrdGT1c, UrdGT2, AknK, AknS, DesVI, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof. Also in this method, the NTP is ATP. Preferably the GalK variant is Y371H, M173L or Y371H-M173L. This method may be carried out in vitro or in a host cell. When the method is carried out in a host cell, preferably, the host cell is a bacterium. More preferably, the host cell is selected from the group consisting of E. coli and S. lividans. Also, in this method the biomolecule capable of being glycosylated is selected from the group consisting of natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, hybrids consisting of one or more these components, analogs and bioactive aglycons thereof. Furthermore, the glycosylated biomolecule is further incubated with at least one chemoselectively ligatable moiety, such that at least one chemoselectively ligated compound is produced.

Following examples depict preferred embodiments of the present invention and are for illustrative purposes only. These examples should not be deemed to narrow the scope of the present invention.

Materials and Methods

Materials. E. coli strains XL1-blue and BL21-Gold (DE3) were purchased from Stratagene (La Jolla, Calif.). The template plasmid pGalK has been previously described. Expression vector pET15b was from Novagen (Madison, Wis.). All reagent grade chemicals and enzymes were purchased from Promega (Madison, Wis.), Sigma (St. Louis, Mo.), Fisher/Acros Organics (Hanover Park, Ill.), or Fluka (Milwaukee, Wis.).

Chemical synthesis of L-idose and D-idose. The syntheses of D- and L-idose followed literature preparations. Gene diversification, library preparation and characterization. For the gene library used, error-prone PCR (epPCR) was accomplished under the following conditions: 25 mM $MgCl_2$, 0.1 mM $MnCl_2$, 0.2 mM (each) dATP and dGTP, 1.0 mM (each) dCTP and dTTP, 500 pg template plasmid pGalK, 40 pmol (each) primers 5"-CTTGGTTATGCGGGTACTGC-3"(SEQ ID NO: 15) and 5 "-TCCCGCGAAATTMTACGAC-3"(SEQ ID NO: 16), 5U Taq DNA-polymerase in the buffer supplied with the enzyme, in a total volume of 100 μl using the following thermocycle parameters: initial denaturation, 5 min, 94°C.; amplification, 30 cycles, 94°C. for 0.5 min, 54°C. for 0.5 min, 72°C. for 1.5 min; terminal hold, 5 min at 72°C. The amplification products were digested with BamHI/XbaI, purified on an agarose gel (0.8% w/vol), eluted using the QIAquick extraction kit (QIAGEN, Valencia, Calif.), ligated into appropriately digested pET 15b, to directly transform E. coliXL1 blue. Plasmids were isolated from randomly picked colonies (~20 representatives for each library generated) and sequenced on an ABI 310 automatic DNA sequencer (PerkinElmer, Foster City, Calif.). Upon verifying the desired mutation rate, all transformants were pooled, cultured overnight, the collectively recovered plasmids used to transform E. coli BL21-Gold (DE3) and the library processed as described below.

Bacterial fermentation. E. coli was grown in LB medium, supplemented with ampicillin (100 μL $mL^{-1}$ final) under standard conditions. For expression of GalK enzyme library members, individual transformants were grown as 1 mL miniature cultures in 96 deep well blocks overnight as seed cultures, then replicated in fresh medium (2%, vol/vol), afterwards added 15% (vol/vol) glycerol, mixed, and stored at 80° C. The replicated cultures were grown to an $OD_{600}$ ~0.7, protein expression was then induced by adding 1 mM IPTG (final), for 2 hours, then harvested by centrifugation (10 min, 3000×g). The cell paste was frozen at 20° C. Upon thawing the harvested expression cultures, the biomass of each well was resuspended in 50 μL NPI-buffer (50 mM $NaH_2PO_4$, 300 mM NaCl, pH 8.0) to which was then added 70 μL NPI-buffer supplemented with 1 μL Lysonase (Novagen, Madison, Wis.) for lysis. Cell debris was collected by centrifugation (10 min, 3000×g), and 20 μL of the clear supernatant, containing ~0.5 μg of the expressed GalK variant on average, was used for each kinase assay.

Library screening. Enzymatic reactions and assays were set up and read in 96 well format on a Biomek FX automated liquid handling workstation (Beckman Coulter, Fullerton, Calif.) fitted to a Fluostar Optima plate reader (BMG, Durham, N.C.). The in vitro enzymatic reactions and assays followed the protocol published previously, slightly modified for automated liquid handling: 150 μL sugar solution (8 mM final) and 12 μL ATP/$Mg^{2+}$ solution (20 mM/5 mM final) were mixed, preincubated at 37° C. for 5 min, then 20 μL of the cleared supernatant was added, and the reaction incubated at 37° C. for an additional 2 h. To assay the phosphorylation reactions, 50 μL of the enzymatic reaction were taken at time zero and after the 2 h incubation, mixed with 100 μL of 3,5-dinitrosalicylic acid (DNS) reagent, heated at 100° C. for 5 min, then immediately chilled on ice for 2 min. Assays were run as endpoint measurements following the decrease in absorption ($\lambda$=575 nm, $\epsilon$=758 $M^{-1}$ $cm^{-1}$).

Characterization of GalK Mutants. The GalK mutant Y371H was overexpressed and purified following the procedure previously described for wild-type GalK. The fractions containing homogenous Y371H GalK were collected, concentrated and quantified using the Bradford protein assay. The DNS assay was used to assess the substrate specificity of the purified GalK mutant (Y371H) as previously described. Standard curves for each sugar were prepared as described. In order to determine the kinetic data for each active monosaccharide substrate, the sugar concentration was varied over a range of 1-16 mM, under saturating ATP (15 mM). Using the DNS assay, change in absorbance at 575 nm as a function of time was obtained and the initial velocity determined by the slope of the linear phase in the progress curve. The kinetic data was analyzed using Enzyme Kinetics Module software (SSPS, Inc., Chicago, Ill.) as previously described.

Preparative phosphorylation of L-altrose and product characterization. L-altrose (21.6 mg, 0.12 mmol) was dissolved in 15 mL 50 mM sodium phosphate buffer (pH 7.5). To this solution, ATP (125 mg, 0.23 mmol), $MgCl_2 \cdot 6H_2O$ (15.3 mg, 0.07 mmol) were added, the mixture incubated at 37° C. for 5 min, the reaction initiated via the addition of enzyme (Y371H) to a final concentration of 150 μg $mL^{-1}$ and reaction progress monitored by TLC. After completion, the mixture was diluted 5-fold in $ddH_2O$ and applied to a 200 mL anion exchange column (Q-Sepharose fast flow, Amersham, Piscataway, N.J.). The column was eluted with a gradient of 0-400 mM NaCl and the active fraction was collected and evaporated under reduced pressure. The crude product was desalted on a P-2 gel filtration column (The Nest Group, Southboro, Mass.) to give 16.1 mg of purified product (yield: 52%). $[\alpha]_D$=3.5° (c=1, $H_2O$) $^1H$ NMR ($D_2O$): 5.48 (dd, J=8.6, 1.8 Hz, 1H), 4.14 (dd, 5.3, 3.3 Hz, 1H), 3.99 (m, 1H), 3.98 (dd, J=4.3, 1.8 Hz, 1H), 3.91 (d, J=3.3, 1H), 3.89 (m, 1H), 3.84 (dd, J=12.1, 7.8 Hz, 1H); $^{13}C$ NMR ($D_2O$): 94.10, 76.23, 70.70, 69.99, 65.68, 62.21; $^{31}P$ NMR ($D_2O$): 3.77; MS: calculated for $C_6H_{13}O_9P$ 260.0, found m/z 259.0 $[M-H]^-$.

Results and Discussion.

Directed evolution of GalK with expanded specificity. The cloned wild-type galK gene from *E. coli* was subjected to random mutagenesis by epPCR performed over the entire gene. The level of sequence alteration was adjusted to an average of 1.5 amino acid substitutions per enzyme molecule, and verified by DNA-sequencing of corresponding genes. However, epPCR usually results in a more or less strong mutational bias (29, 30, 44) and is therefore not a truly random process. Under the conditions selected, the library contained a transition/transversion ratio of ~3.0, the transitions outnumbering the transversions, and the AT→GC/GC→AT ratio was found to be 2.4. A population of 3,500 GalK variants from this library were evaluated for their ability to accommodate an expanded spectrum of sugar substrates. The inventors' goals were kinase activity toward L-configured sugars (C-5 alteration) or to those with altered substituents at C-6. Unlike most assays in high-throughput campaigns which screen or select toward a single substrate or substrate mimic, the inventors' recently developed DNS assay is universally applicable to all reducing sugars. Consequently, simultaneous screens for a relaxed enzyme specificity were carried out with a set of appropriately selected sugar substrates rather than a one-dimensional single substrate screen of each library member. To first focus upon C-5 and C-6, the set included a single C-5 challenge—L-altrose (Table 1, 16, the C-5 epimer of D-galactose)—and three C-6 challenges—6-deoxy-D-galactose (22, D-fucose), 6-amino-6-deoxy-D-galactose (23) and D-galacturonic acid (24). Of this set, only D-fucose (22) showed any turnover with wild-type GalK, albeit 2.7% that observed for D-galactose (14). Table 1 describes the kinetic data for the ten active substrates of the GalK variant (Y371H).

| | | wild type | | | Y371H | | |
|---|---|---|---|---|---|---|---|
| sugar substrate | | $K_m$* | $k_{cat}$† | $k_{cat}/K_m$‡ | $K_m$* | $k_{cat}$† | $k_{cat}/K_m$‡ |
| 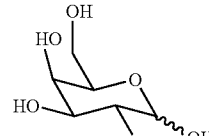 | D-Gal (14) | 2.1 | 108 | 51.4 | 5.6 | 220 | 39.3 |
| 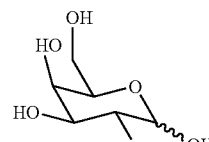 | 2-deoxy-D-Gal (18) | 3.6 | 30 | 8.3 | 4.7 | 200 | 42.6 |
| 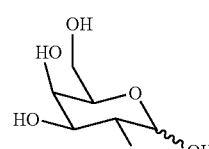 | $D-GalNH_2$ (19) | 2.9 | 11.7 | 4.0 | 8.8 | 260 | 29.5 |
| 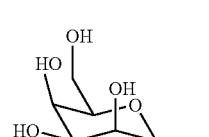 | D-Tal (20) | —§ | —§ | —§ | 2.9 | 45.5 | 15.7 |
| 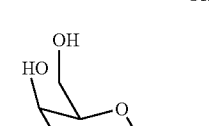 | 3-deoxy-D-Gal (21) | 6.4 | 5.1 | 0.8 | 10.1 | 64.6 | 6.4 |

-continued

| sugar substrate | | wild type | | | Y371H | | |
|---|---|---|---|---|---|---|---|
| | | $K_m$* | $k_{cat}$† | $k_{cat}/K_m$‡ | $K_m$* | $k_{cat}$† | $k_{cat}/K_m$‡ |
| [structure] | 6-deoxy-D-Gal (22) | 4.9 | 2.9 | 0.59 | 8.0 | 101 | 12.6 |
| [structure] | 6-amino-D-Gal (23) | —§ | —§ | —§ | 21.3 | 149 | 7.0 |
| [structure] | D-Galacturonic acid (24) | —§ | —§ | —§ | 3.2 | 58 | 18.1 |
| [structure] | L-Alt (16) | —§ | —§ | —§ | 5.2 | 80 | 15.4 |
| [structure] | L-Glc (25) | —§ | —§ | —§ | 2.7 | 65 | 24.1 |

*mM
†min$^{-1}$
‡mM$^{-1}$ min$^{-1}$
§no conversion

Figure 3:
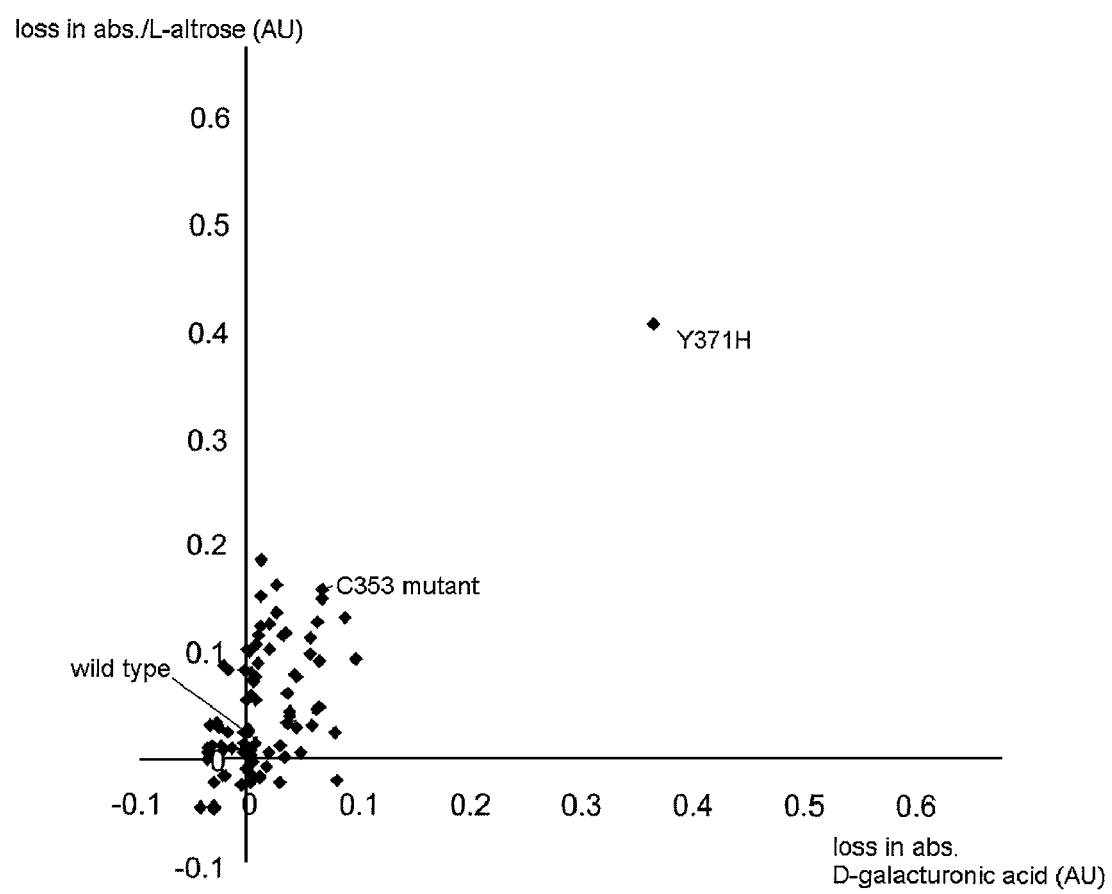
FIG. 3. Provides representative quantitative data for a set of GalK variants, illustrating screen for D-galacturonic acid (X-axis) and L-altrose (Y-axis). The higher the loss in absorption (shown in absorption units (AU), the more active the enzyme variant.

The graphical display of a typical screening result is given in FIG. 3. Surprisingly, after only one round of evolution two GalK variants appeared independently which phosphorylated the C-5/C-6 set of sugars with roughly similar efficiency. Subsequent DNA-sequencing of both GalK variant genes revealed that they were identical in their sequence and carried a single forward mutation, a C→T transition at position 1111 of the wild-type reading frame, which translates into a tyrosine 371 to histidine replacement.

The structure of the Lactococcus (L.) lactis galactokinase was published. Despite a rather low sequence homology to the E. coli GalK (36% identity, 53% similarity) these two kinases clearly share three characteristic footprint motifs, and all amino acid residues found within the catalytic center of the L. lactis galactokinase (R36, E42, D45, D183, and Y233) are invariably present in its E. coli homolog (R28, E34, D37, D174, Y223, respectively), embedded in highly conserved sequence environments. For this reason, the inventors speculate that the equivalent residues also form the catalytic apparatus in the E. coli enzyme. Surprisingly, residue 371 in the E. coli wild-type enzyme, found to be essential for the widened substrate specificity and the activity toward L-configured sugars, does not appear as part of its deduced active site. In the L. lactis galactokinase the $C_\alpha$ of the equivalent amino acid Y385 located within the C-terminal domain β-strand K is ~20 Å from the anomeric carbon of the substrate when bound in the active site. In the L. lactis galactokinase crystal structure Y385 is located in close proximity to C353 (C339 in E. coli GalK). The tyrosine phenolic oxygen is located ~5.5 Å from the cysteine sulfur atom. Interestingly, during the screen, a mutant on position 339 was also discovered with a similarly expanded substrate profile yet low catalytic activity regardless of the sugar (data not shown). This implicates a potential Y385-C353 (Y371-C339 in E. coli GalK) side chain interaction may play a role in stabilizing this structure and thereby dictate substrate specificity. While an induced fit model has not been previously put forth for this class of enzyme, such "gate-keeping" interactions are known to occur in other enzymes devoted to carbohydrate metabolism, such as hexokinase.

Characterization of the GalK variant (Y371H). To determine the substrate specificity of the Y371H GalK variant, a sugar library of twenty putative substrates was tested with the purified enzyme. For each sugar, both the DNS assay and thin layer chromatography were used to monitor the reaction progress and control assays in the absence of enzyme or sugar were performed in parallel. The mutant GalK demonstrated the ability to turn over compounds 14, 16, 18-25 (Table 1), strikingly expanding the overall substrate scope compared with wild-type E. coli GalK. The kinetic parameters of the mutant enzyme with all active substrates (14, 16, 18-25) were determined using the DNS assay and compared with wild-type GalK activity. These kinetic studies also revealed, as expected, the evolved enzyme remains an efficient catalyst with D-galactose ($k_{cat}$=220 min$^{-1}$, $K_m$=5.6 mM) and displays remarkably enhanced $k_{cat}$ values for all the previously known substrates for wild-type GalK (14, 18, 19, 21, 22), the affinity for which is slightly reduced in all cases.

While most in vitro evolution projects require repeated rounds of random mutation and/or recombination to generate the desired activity, a leap in GalK catalytic activity and substrate selectivity was accomplished in the initial round of random mutagenesis. Other recent similar examples of single forward mutations leading to a catalytic shift include, for example, the *Arabidopsis thaliana* cycloartenol synthase or yeast lanosterol synthase, or the adipyl acylase evolved from a *Pseudomonas* glutaryl acylase. From an analysis of the GalK substrate specificity profiles, one can begin to construct a loose structure-activity requirement for both wild-type enzyme and the corresponding Y371H mutant. Specifically, wild-type GalK displays a stringent requirement for the substrate galactose architecture from C-3 through C-6 and is capable of limited flexibility toward substitution at C-2. Yet, it is interesting to note these stringent requirements, with the exception of the extensive contacts at C-4, are not readily apparent in the *L. lactis* GalK active site structure. In contrast to wild-type GalK, the Y371H mutation retains primarily only the stringent requirement for the C-4 galactose architecture with an enhanced substrate specificity flexibility at all other positions of the sugar. Remarkably, with essentially all substrates accepted, an enhancement of catalytic efficiency was observed in the Y371H mutant, the enhancement ranging from 5- to 22-fold. The only exception was the wild-type substrate galactose for which the catalytic efficiency was decreased slightly in comparison to wild-type GalK, albeit $k_{cat}$ in this case was also increased 2-fold.

Figure 4:
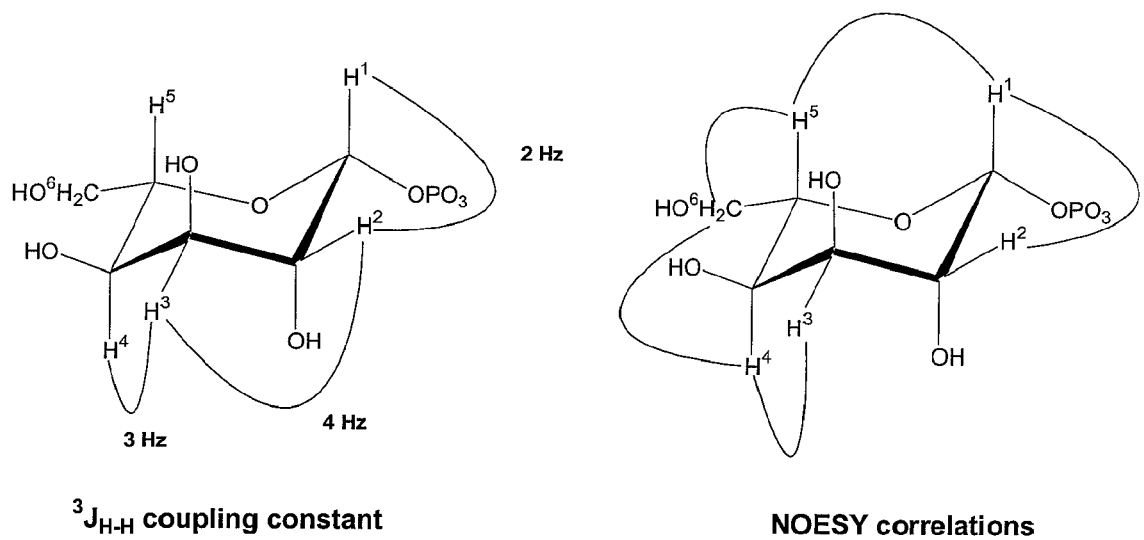
FIG. 4. Provides $^3J_{H-H}$ coupling patterns and NOESY correlations for the GalK Y371H product β-L-altrose-1-phosphate.

Confirmation of L-sugar conversion. The substrate specificity studies have demonstrated GalK variant Y371H to be a D/L-unspecific sugar kinase. To confirm the evolved enzyme retains regio- and stereoselectivity with L-sugar substrates, a representative L-sugar reaction product was further characterized. Specifically, a small-scale preparative phosphorylation reaction was performed with L-altrose (21.6 mg, 0.12 mmol). The DNS assay indicated 91% of L-altrose conversion within four hours. Product isolation was readily achieved by anion exchange chromatography, and the yield of purified product was ~52%. The purified product was characterized by 1H and $^{13}$C NMR from which H—H coupling and NOESY data confirmed the product to be β-L-altrose-1-phosphate in a $^1C_4$ conformation (FIG. 4). In particular, $^3J_{H-H}$ coupling data showed two typical axial-equatorial couplings (H1-H2, H3-H4) and one equatorial-equatorial coupling (H2-H3). NOESY data also revealed the anticipated correlations consistent with this structure (H1-H2, H1-H5, H3-H4, H4-H6 and H5-H6). Based upon this data the inventors propose the Y371H mutant must bind and phosphorylate L-altrose in the same $^4C_1$ conformation as D-galactose (FIGS. 2c and 2d) (38) the product of which subsequently rapidly equilibrates to the more stable $^1C_4$ conformation upon release from the enzyme.

Implications for In Vitro Glycorandomization

Apart from total synthesis, current approaches to alter glycosidic structures include, for example, combinatorial biosynthesis or in vitro biocatalysis. Combinatorial biosynthesis primarily relies on in vivo diversification via genetic engineering of involved sugar biosynthetic pathways. Mendez, C., & Salas, J. (2001) *Trends Biotechnol.* 11, 449-456. However, combinatorial biosynthesis is significantly limited by enzyme specificity which substantially biases the ultimate extent of diversity accessible. In contrast, IVG presents a significant advantage by providing a truly unbiased library of activated sugars to utilize for drug lead glycosylation. The present advent of kinase-enhanced IVG not only simplifies the upstream availability of sugar-1-phosphates for IVG but also potentially opens the door to in vivo applications of glycorandomization. Specifically, the expression of a tandem promiscuous sugar-1-kinase (GalK) and nucleotidylyltransferase ($E_p$) in a given organism, presents the prospect of generating a library of NDP-sugars in situ. As such, the present invention provides the foundation for eventually glycorandomizing a variety of clinically important secondary metabolites in vivo to rapidly enhance drug discovery efforts. Such techniques are also described in the U.S. Patent Publications 2003/0055235A1 and 2003/0068669A1, and International Publications WO02079150 and WO0248331, which are incorporated herein by reference in their entirety for all purposes.

In one embodiment of the present invention, promiscuous sugar-1-kinase (GalK) may be used for synthesizing NDP-sugars. The method of synthesizing comprises the steps of incubating a nucleotide triphosphate (NTP) and a D or L sugar in the presence of a GalK variant such that a sugar phosphate is produced. The sugar phosphate is further incubated with a nucleotidylyltransferase, such that a NDP-sugar is produced. Various anomeric sugars may be used to form the sugar phosphate, including the D or L sugars such as D-galactose, 2-deoxy D-galactose, D-galactose-amine, D-talose, 3-deoxy-D-galactose, 6-deoxy-D-galactose, 6-amino-D-galactose, D-galacturonic acid, L-altrose and L-glucose.

In a preferred embodiment, the nucleotidylyltransferase is Ep or a mutated variant thereof. The mutated Ep variant includes Ep that is mutated at one or more amino acids V173, G147, W224, N112, G175, D111, E162, T201, I200, E199, R195, L89, L89T, L109, Y146 and Y177. In one preferred embodiment the method may be carried out in vitro. In another preferred embodiment, the method is carried out in a host cell. The host cell may be a bacterium. Further, the host cell may be selected from the group consisting of *E. coli* and *S. lividans*.

Another preferred embodiment of the present invention provides a method of producing a glycosylated biomolecule containing at least one sugar moiety. The method comprises the steps of incubating a nucleotide triphosphate (NTP) and a D or L sugar in the presence of a GalK variant, whereby a sugar phosphate is produced; incubating the sugar phosphate with a nucleotidylyltransferase, whereby a NDP-sugar is produced; and incubating the NDP-sugar with a biomolecule capable of being glycosylated in the presence of a glycosyltransferase, such that a glycosylated biomolecule is produced. In a preferred embodiment, the glycosyltransferase is selected from the group consisting of CalB, CalE, CalN, CalU, Gra orfl4, Gra orf5, LanGT1, LanGT2, LanGT3, LanGT4, MtmGI, MtmGII, MtmGTIII, MtmGTIV, NovM, RhlB, Rif orf 7, SnogD, SnogE, SnogZ, UrdGT1a, UrdGT1b, UrdGT1c, UrdGT2, AknK, AknS, DesVI, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof. In another preferred embodiment, the biomolecule capable of being glycosylated is selected from the group consisting of natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, hybrids consisting of one or more these components, analogs and bioactive aglycons thereof. In yet another preferred embodiment, the glycosylated biomolecule is further incubated with at least one chemoselectively ligatable moiety, such that at least one chemoselectively ligated compound is produced. Exempletive chemoligation techniques are described in the U.S. patent application Ser. No. 10/670,073 "Glycorandomization and Production of Novel Vancomycin Analogs", filed on Sep. 24, 2003, which is incorporated in its entirety by reference for all purposes.

The inventor has applied directed enzyme evolution and relied upon a high throughput galactokinase (GalK) assay (DNS assay) for the screening of diverse E. coli GalK variant libraries generated via error-prone PCR. From this approach, one particular GalK mutant (Y371H) demonstrated remarkably widened substrate flexibility toward C-2, C-3 and C-5 substitutions of D-galactose. Yet, the mutant retained a stringent requirement for the axial C-4 galactose architecture. The recently solved L. lactis GalK crystal structure suggested two

TABLE 2

|  | D-Gal (29) $K_m$ mM | D-Gal (29) $V_{max}$ mM min$^{-1}$ | D-Glc (27) $K_m$ Mm | D-Glc (27) $V_{max}$ mM min$^{-1}$ | L-Alt (21) $K_m$ mM | L-Alt (21) $V_{max}$ mM min$^{-1}$ |
|---|---|---|---|---|---|---|
| WT GalK | 2.1 (±0.4) | 1.5 (±0.5) | — | — | — | — |
| M173L | 5.9 (±0.8) | 1.9 (±0.6) | 2.6 (±0.5) | 0.02 (±0.01) | — | — |
| Y371H | 5.6 (±0.3) | 2.2 (±0.6) | — | — | 6.0 (±0.9) | 0.16 (±0.04) |
| M173L-Y371H | 4.6 (±0.7) | 2.3 (±0.4) | 4.0 (±0.6) | 0.02 (±0.01) | 6.3 (±1.1) | 0.07 (±0.03) |

EXAMPLE II

Glycorandomization (FIG. 5a), a process centered upon the inherent promiscuity of secondary metabolite-associated glycosyltransferases, is one of the latest promising developments toward this important goal. Critical to the success of glycorandomization has been the ability to engineer and/or evolve two additional promiscuous enzymes—anomeric kinases and nucleotidylyltransferases. Taken together with the many elegant methods to synthesize monosaccharide libraries and the intrinsic substrate flexibility of many secondary metabolite-associated glycosyltransferases, this two-enzyme short activation pathway allows one to rapidly diversify the sugars attached to complex natural products. The glycorandomization process is further enhanced via a final diversification step which relies upon the use of downstream chemoselective ligation.

Figure 5:
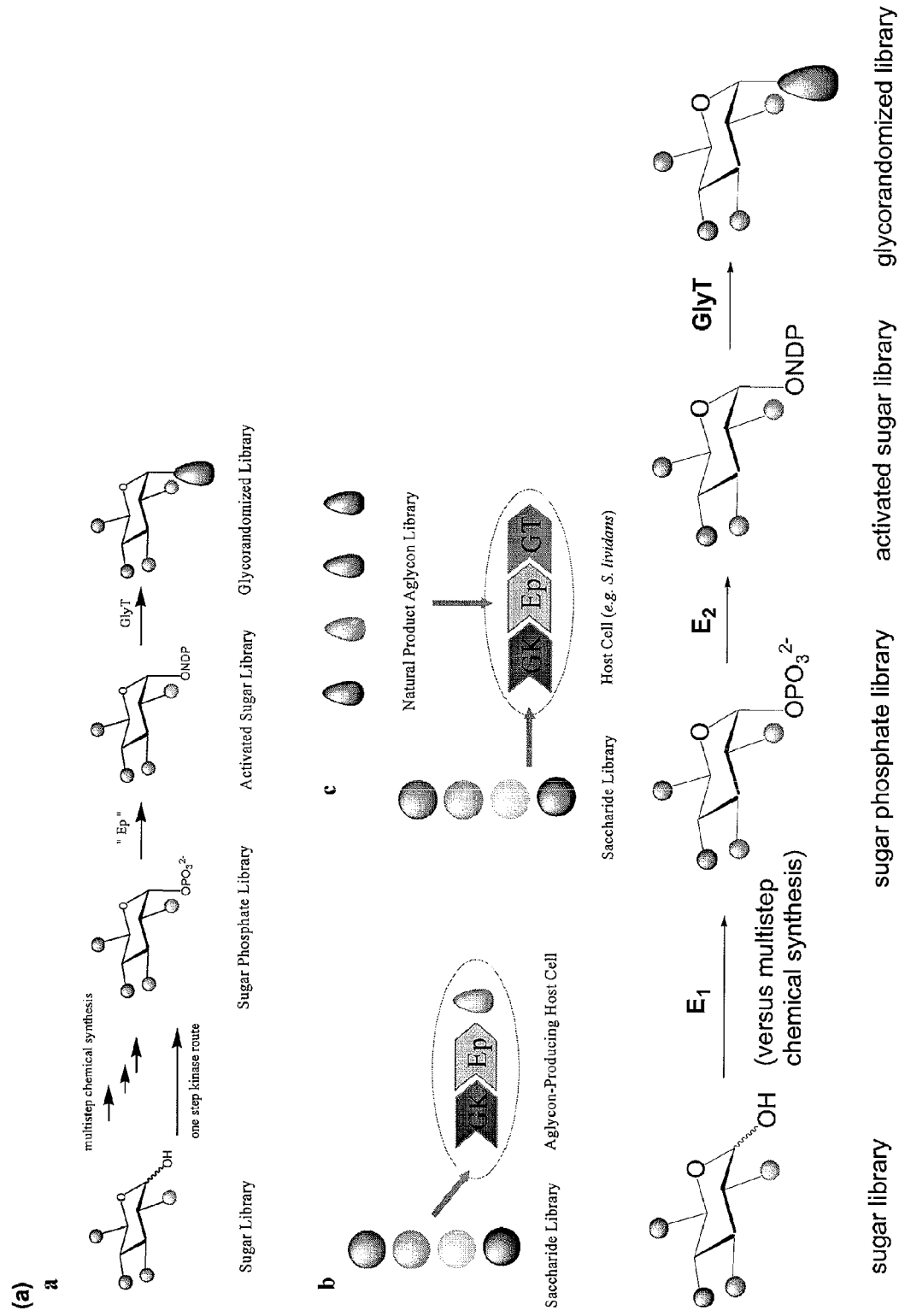
FIG. 5. Glycorandomization overview and two potential scenarios for an in vivo approach. (a) In vitro glycorandomization utilizes two enhanced enzymes—$E_1$ (a general kinase) and E2 (a general nucleotidylyltransferase)- to generate NDP-sugar substrate libraries to be utilized by a flexible natural product-associated glycosyltransferase (GlyT). (b) In vivo glycorandomization scenario I—feeding monosaccharides to a natural product-producing host engineered to express the 'NDP-sugar factory'. In this scenario, both the aglycon and glycosyltransferase are provided by the bacterial host. (c) In vivo glycorandomization scenario II—feeding monosaccharides and aglycons to a non-producing host engineered to express the 'NDP-sugar factory' and an appropriate glycosyltransferase or glycosyltransferase library.
Figure 5:
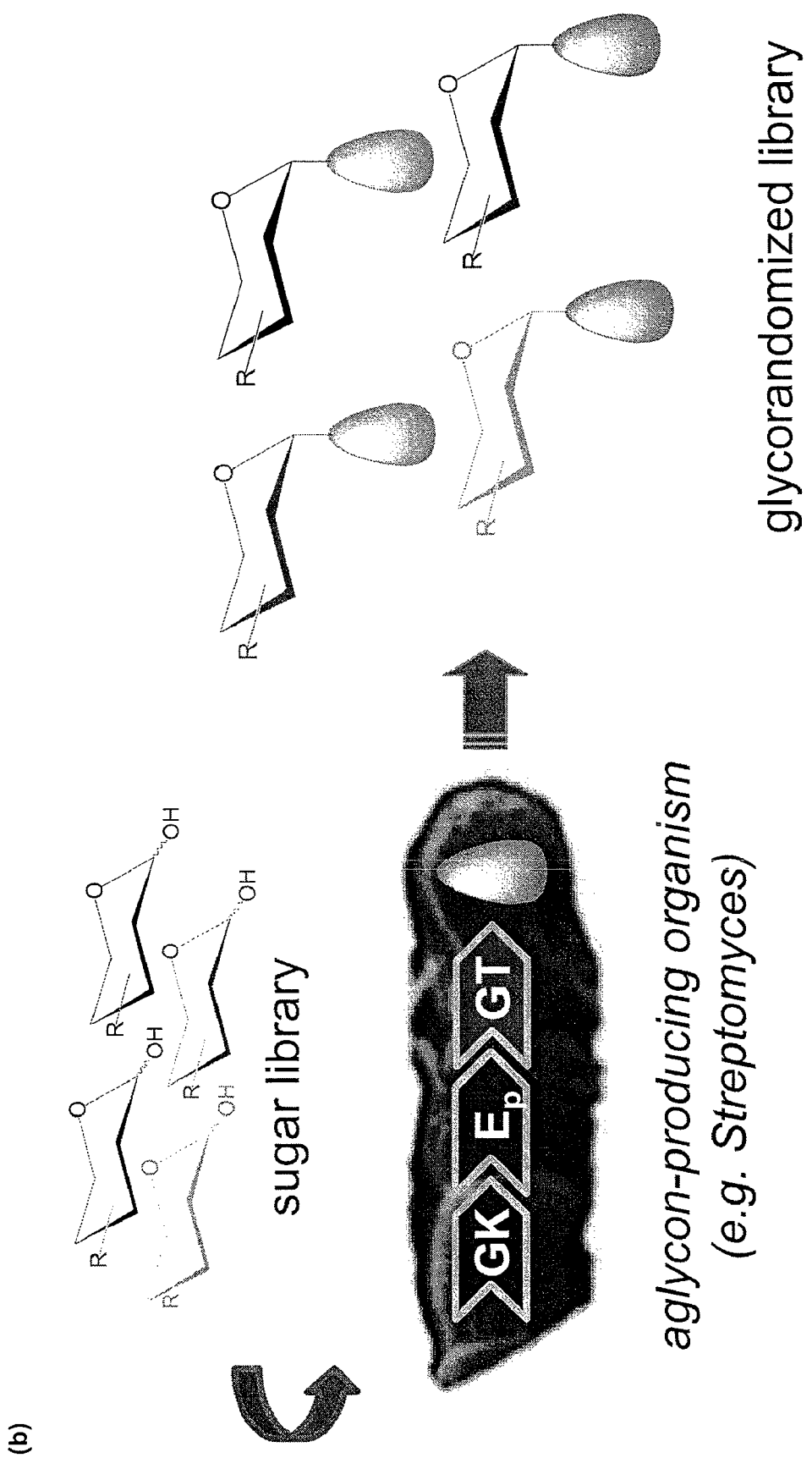
Figure 5:
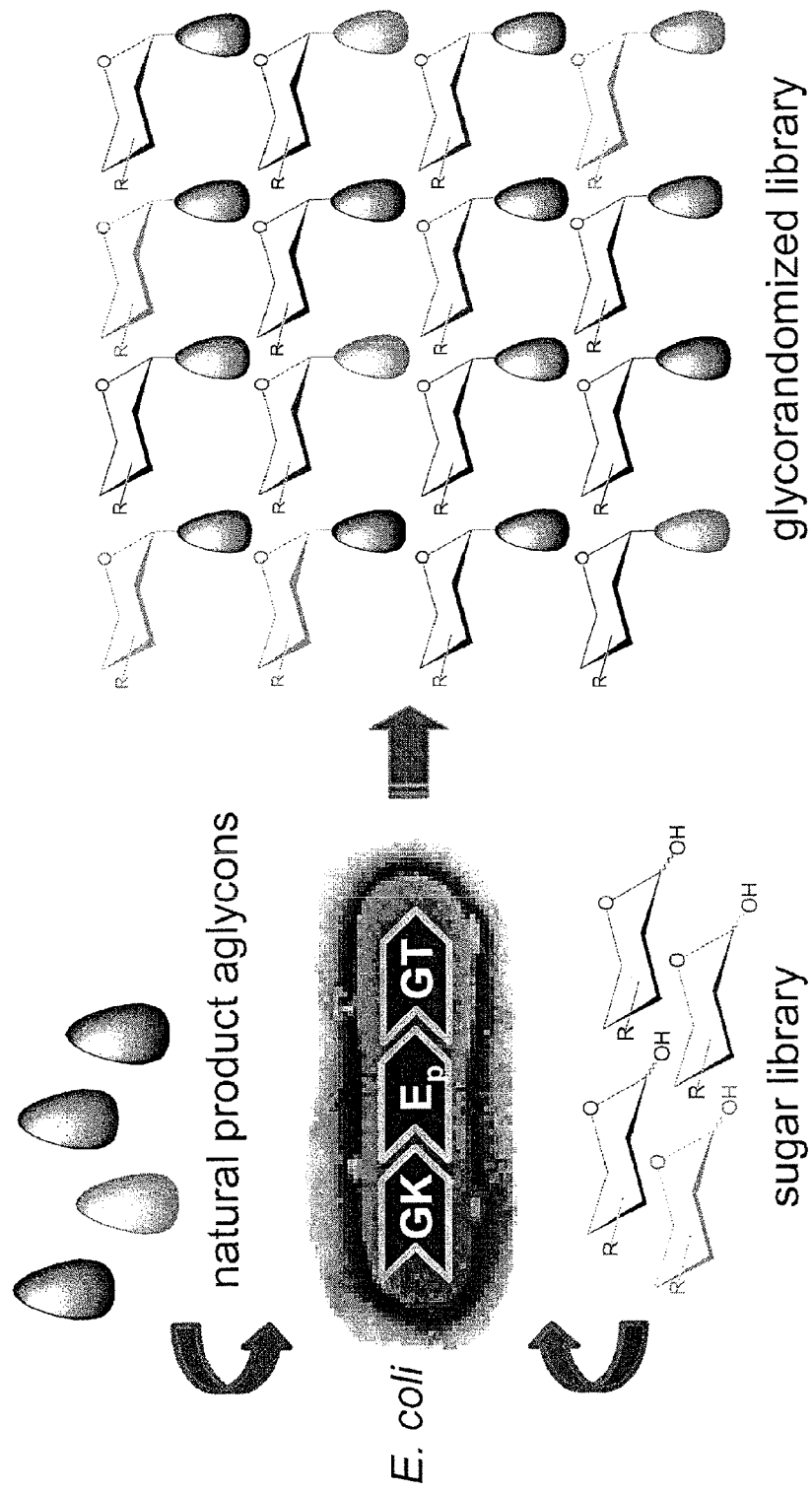

Cumulatively, the successful demonstration of in vitro glycorandomization, the observations that functional NDP-sugar pathways can be reassembled in prokaryotes, and the fact that natural and 'unnatural' endogenous sugars are processed in vivo by both prokaryotes and eukaryotes, present the foundation from which to approach in vivo glycorandomization. For example, the expression of a tandem promiscuous sugar-1-kinase (GalK) and nucleotidylyltransferase ($E_p$)—essentially an unnatural NDP-sugar factory—in a natural aglycon-producing host (e.g. the erythromycin-producing Saccharopolyspora) should present the prospect of generating a glycorandomized library in situ, the glycorandomized metabolite output of which is controlled by monosaccharides being fed to the strain (FIG. 5b). Alternatively, expression of the tandem two gene 'NDP-sugar factory' genes in a non-producing host (e.g. S. lividans or E. coli) which expresses a given glycosyltransferase (or glycosyltransferase library), should also provide a vehicle to accomplish glycorandomization via feeding the host with appropriate aglycon acceptors and unnatural sugar donors (FIG. 5c). The key to either in vivo scenario is the ability of unnatural sugars to enter the host and serve as efficient substrates of the first enzyme of the short activation pathway (the flexible anomeric kinase). Toward this goal, a kinase able to process sugars bearing unique mass signatures and/or reactive handles would, in addition to further enhancing library diversification, greatly simplify the final analysis of in vivo access and activity.

highly conserved active-site residues (Asp-37 and Tyr-223 in E. coli GalK) are responsible for hydrogen-bonding with this C-4 axial hydroxyl group of the substrate. Yet, saturation mutagenesis at these two critical positions in the E. coli enzyme failed to provide mutants with enhanced C-4 sugar flexibility while a parallel study revealed the L. lactis wild-type GalK and Y385H orthologs to surprisingly display weak activity toward the C-4 epimer, glucose.

Herein the inventor reports a structure-activity model, based upon the L. lactis active site and its ability to weakly utilize glucose, led to a specific engineered E. coli M173L mutant GalK with enhanced C-4 and C-6 promiscuity. Moreover, a combination of the favorable structure-based (M173L) mutation with the beneficial mutation previously discovered via directed evolution (Y371H) drastically exceeds an additive enhancement for both C-4 and C-6 substitutions. Most importantly, the additional unnatural sugar substrates accessed by this unique double mutant allowed the unique opportunity to assess whether unnatural sugars can enter a bacterial host and serve as efficient substrates of the first enzyme of the glycorandomization pathway (the flexible anomeric kinase). Specifically, feeding of the unique substrate 6-azido-6-deoxy-galactose (22) or 6-azido-6-deoxy-glucose (46) to an E. coli host engineered to express M173L-Y371H-GalK followed by the rapid fluorescent labeling of substrates and products via Huisgen 1,3-dipolar cycloaddition revealed the desired efficient sugar-1-phosphate production in vivo. This result stands as a key first step in demonstrating the concept of in vivo glycorandomization.

Materials and Methods

Materials. The syntheses of 4-azido-4-deoxy-D-galactose (21), 6-azido-6-deoxy-D-galactose (22), 6-chloro-6-deoxy-D-galactose (23), 6-bromo-6-deoxy-D-galactose (24), 4-deoxy-D-galactose (25), 6-hydroxymethylene-D-galactose (32), 3-deoxy-D-galactose (34), 6-amino-6-deoxy-D-galactose (35), 6-deoxy-6,6-difluoro-D-galactose (40), were reported previously while other monosaccharide compounds 26-31, 33, 36-39, 41, 42, 45, 47 and 48 were purchased from Sigma (St. Louis, Mo.), Fisher/Acros Organics (Hanover Park, Ill.), or Fluka (Milwaukee, Wis.). E. coli strains XL1-blue and BL21 (DE3) were purchased from Stratagene (La Jolla, Calif.). Expression vector pET15b was purchased from Novagen (Madison, Wis.). Enzymes were purchased from Promega (Madison, Wis.).

Chemical Synthesis. For chemical synthesis of 6-thio-6-deoxy-D-galactose 43, 6-thio-6-deoxy-D-glucose 44, 6-azido-6-deoxy-D-glucose 46, and 5-dimethylaminonaphthalene-1-(N-(5-propargylamidepentyl))-sulfonamide 50, see supporting methods, which is published as supporting information on the PNAS web site.

Structure Modeling. The PDB file for the crystal structure of *L. lactis* wild type GalK was obtained from the Protein Data Bank, Research Collaboratory for Structural Bioinformatics, Rutgers University, New Brunswick, N.J. (available on the Rutgers University website). The structure modeling was accomplished using Swiss-PdbViewer software (Version 3.7).

Site-specific Mutagenesis. The GalK M173L single mutant and M173L-Y371H double mutant were generated using the QuikChange II Site-Directed Mutagenesis Kit from either wild-type or Y371H template, respectively (Stratagene). The corresponding mutated plasmids pGalKM173L and pGakKMLYH were constructed by using PfuUltra™DNA polymerase for mutagenic primer-directed replication from pGalK or pGalKY371H template, respectively, using a pair of mutagenic primers (5'-GTMCTGCGG-GATCCTGGATCA- GCTAATTTCCG-3'(SEQ ID NO: 17) and 5'-CGGMATTAGCTGATCCAGGATCCCG-CAGTTAC-3'(SEQ ID NO: 18)). Amplification was accomplished under the following conditions: 5 μL of 10 × reaction buffer, 40 ng template DNA, 120 ng of each oligonucleotide primer, 1 .mu.L dNTPs mixture (2.5 mM), 2.5 U of PfuUltra™high-fidelity DNA polymerase, in a total volume of 50 μL ddH$_2$O (thermocycler parameters: initial denaturation, 2 min at 95° C.; amplification, 12 cycles, 0.5 min at 95°C., 1 min at 55° C., 6.5 min at 68° C.; terminal hold, 5 min at 68° C.). The amplified plasmids were treated with DpnI to digest the parental DNA template and the mutated prodigy plasmid subsequently used to transform *E. coli*XL1-blue. The desired point mutation was verified by sequencing.

Characterization of GalK Mutants. The GalK mutants Y371H was overexpressed following the procedure previously described for wild-type *E coli* GalK, while the overexpression of mutants M173L and M173L-Y371H were accomplished at 16° C. as described for *L. lactis* GalK. The mutant enzymes were purified by using metal affinity chromatography on Ni-NTA Spin Columns (QIAGEN, Valencia, Calif.) and fractions containing homogenous protein were collected, concentrated and quantified using the Bradford protein assay. The DNS assay was used to assess the substrate specificity of the purified GalK mutants as previously described. A library of 45 different sugars was screened with each mutant (M173L, Y371H and M173L-Y371H). For each sugar, the DNS assay was used to monitor the reaction progress and control assays in the absence of enzyme or sugar were performed in parallel. Standard curves for each sugar were prepared as described. To assess general percent conversion, each reaction contained 15.0 (M enzyme, 8 mM sugar, 14 mM ATP and 3.5 mM MgCl2. The reactions were incubated at 37° C. for 3 hrs after which the reactions were quenched with MeOH, centrifuged (10 min, 12,000 rpm) and then the supernatant (diluted 20-fold) submitted for LC-MS and MS/MS analysis. For monosaccharide kinetic data determination, the sugar concentration was varied over a range of 1-8 mM, under saturating ATP (14 mM). Reaction progress was assessed via the DNS assay, wherein a change in absorbance at 575 nm as a function of time was obtained and the initial velocity determined by the slope of the linear phase in the progress curve. The kinetic data was analyzed using Enzyme Kinetics Module software (SSPS, Inc., Chicago, Ill.) as previously described.

In Vivo Conversion Analysis. The GalK double mutant pGalKMLYH-*E. coli* was overexpressed at 16° C. via induction of a 40 mL of culture at an OD$_{600}$ ~0.7 with IPTG (1 mM). The induced and the cultures were incubated with shaking (140 rpm) for 1 hr and 100 mM 22 or 46 was added to the culture to a final concentration of 4 mM. The cultures were further incubated at 16° C. with shaking (140 rpm) for 16 hr. To assess bioconversion, the cells were harvested by centrifugation (15 min, 12,000 rpm) and the recovered cell pellet (380 mg) washed twice with sodium phosphate buffer (20 mL), frozen, thawed and resuspended in H$_2$O:MeOH (1:1). The resuspended solution was heated at 100° C. for 15 min and then sonicated 5×45 sec on ice. Cell debris was collected by centrifugation (15 min, 12,000 rpm) and lyophilized to give the pale white solid (18 mg). To a solution containing all the crude product in 160 μL of H$_2$O:MeOH (1:1) was added 10 pmol 50 and 3.2 pmol of CuI, followed by heating to 50° C. for 24 hours. The reaction mixture was subsequently centrifuged to remove CuI and the supernatant (diluted 2-fold) directly analyzed by HPLC and LC-MS calculated for $C_{26}H_{37}N_6O_{11}PS$ 672.20, found m/z $[M+H]^-$ 671.20.

Results and Discussion

Figure 6:
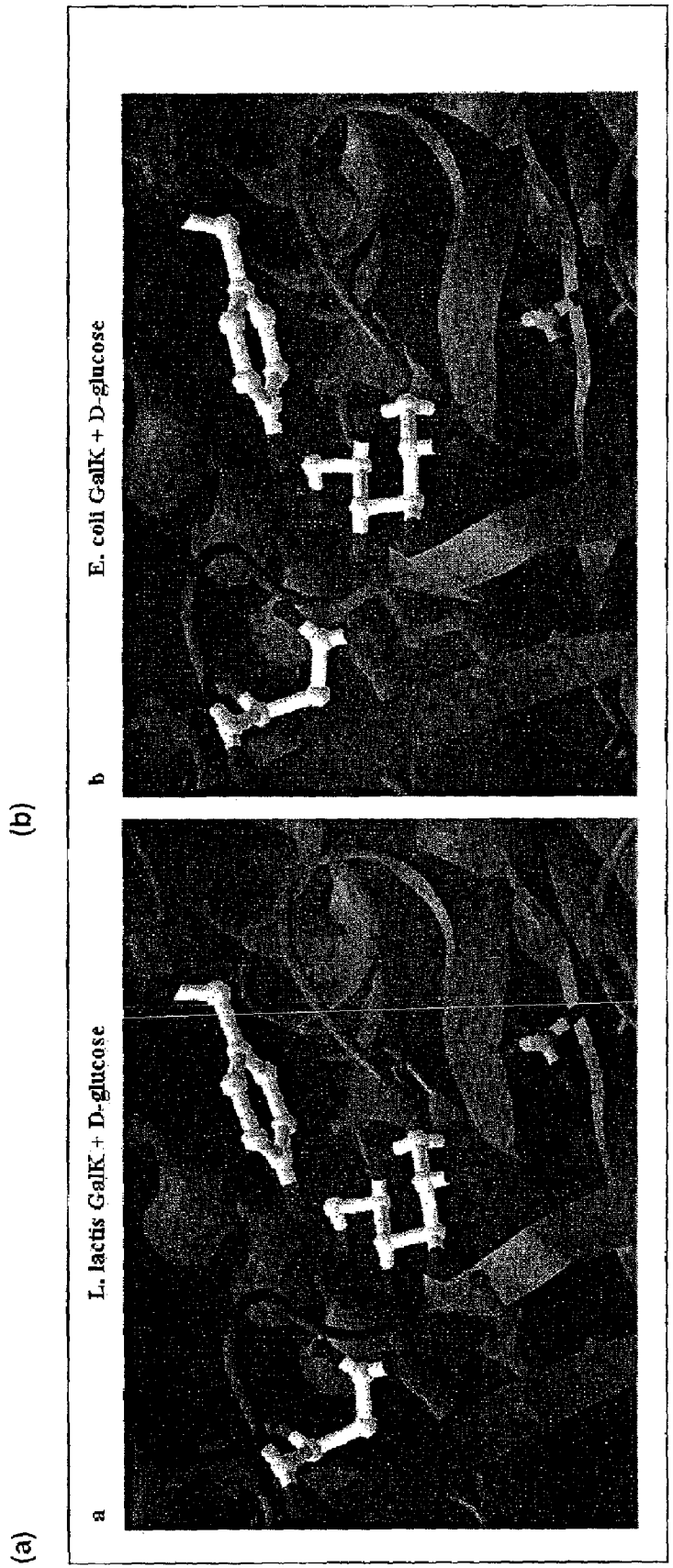
FIG. 6. Comparison of D-glucose docked within the active site of *L. lactis* GalK and homology-model of *E. coli* Gal K. (a) Wild type *L. lactis* GalK bound to D-Glc. (b) L182M (the homology model for *E. coli* GalK active site) with D-Glc.

Structure-basis for Engineering GalKs with Expanded Specificity. Prior to any available GalK structural information, the directed evolution of *E. coli* GalK presented a general sugar anomeric kinase with widened flexibility primarily at C-5 and C-6 of the sugar substrate. Interestingly, all C-4-modified derivatives tested in this study failed as substrates for the evolved catalyst. In contrast, the recent analysis of the *L. lactis* wild-type GalK revealed in vitro conversion of various C-4-modified analogs, including 4-azido-4-deoxy-D-galactose (21), 4-deoxy-D-galactose (25) and D-glucose (27). The recent structure elucidation of *Lactococcus lactis* GalK potentially allows for a molecular level assessment of this surprising C-4 specificity distinction between the *E. coli* and *L. lactis* enzymes. With the *L. lactis* structure as a template, the sequence alignment of the *E. coli* and *L. lactis* GalKs revealed one clear difference among the sugar-binding pockets. Specifically, Leu-182 in *L. lactis* GalK is near to the C-4 carbon atom of galactose (3.85 Å) and, based upon sequence alignment, this residue is replaced by Met-173 in *E. coli* GalK. A model of the C-4 epimer of galactose (D-glucose) within the *L. lactis* active site predicts the Glc-C-4 equatorial hydroxyl to be 3.79 Å from the Y methyl of Leu 182 (FIG. 6a). However, the identical model in which Leu-182 has been replaced by Met (to mimic the *E. coli* GalK active site) revealed the same Glc-C-4 equatorial hydroxyl to be 1.72 Å from Met sulfur (FIG. 6b). Thus, this model clearly suggests Met 173 in *E. coli* GalK may exclude glucose and thereby limit sugar C-4 specificity to galacto-configured substrates. Moreover, given the close proximity of the sugar C-6 hydroxyl to Met in this structural model (2.85 Å) (FIG. 6b), the inventors believe that M-173 in *E. coli* GalK may also limit C-6 variation.

Figure 7:
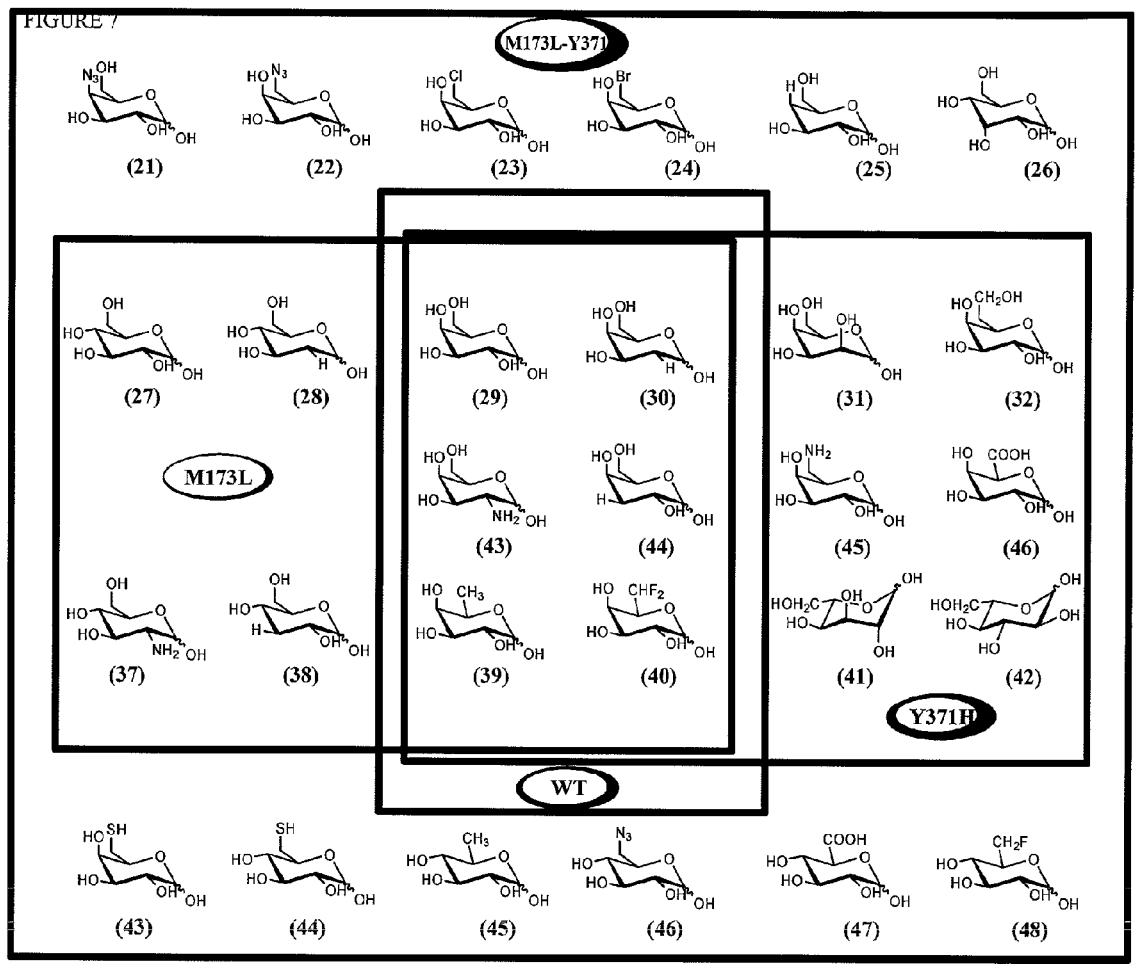
FIG. 7. 'Natural' and 'unnatural' substrates of wild-type GalK and GalK mutants (M173L, Y371H and M173L-Y371H).
Figure 8:
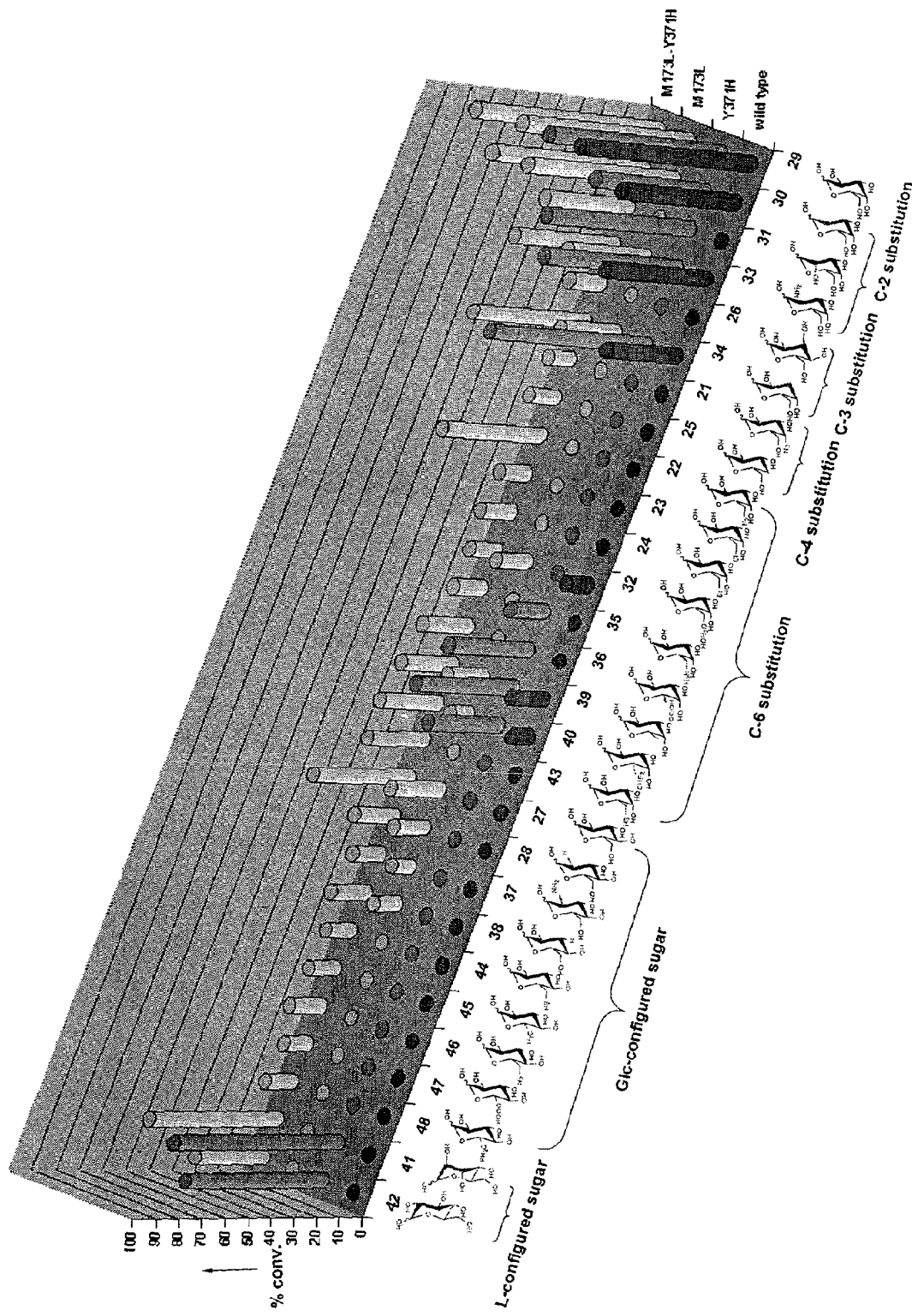
FIG. 8 Percent conversion of sugar substrates by wild-type and mutant GalKs. For each enzymatic reaction: [sugar]=8 mM, [ATP]=14 mM, [MgCl$_2$]=3.5 mM, [enzyme]=15.0 μM and reaction time=180 min.

Characterization of Engineered *E. coli* GalK Mutants. To test the above hypothesis, a single *E. coli* GalK M173L mutant was generated and screened against a panel 45 potential sugar substrates. As predicted, the *E coli* M173L engineered mutant displayed moderate D-glucose 27 activity (20% conversion in 3 hr). Moreover, three additional D-gluco-configured structures 28, 37, 38 (FIGS. 7 and 8), which were not substrates of wild-type *E. coli* GalK (or the evolved *E. coli* Y371H mutant), were also substrates of the new structure-based variant. While these studies clearly revealed the structure-based M173L mutant to accept a substrate set distinct to that of the previously evolved Y371H mutant, in contrast to the structural model described above, both mutants failed in the presence of substrates presenting even moderate C-6 bulk such as 6-azido-6-deoxy-galactose 22 or 6-azido-6-deoxy-D-glucose 46. In an attempt to further generalize the sugar kinase activity, an *E. coli* double M173L-Y371H mutant was examined. Remarkably, not only did this double mutant retain the activity of both corresponding single mutants, but this prodigy demonstrated a substantial degree of kinase activity toward a variety of new structures (21-26, 43-48). Most of the new substrates share modifications at C-4 and/or C-6, with many of D-gluco origin. It is also noteworthy that three among this new substrate set are azidosugars (21, 22 and 46), thereby setting the stage for rapid analysis of in vivo bioconversion via post-bioconversion labeling of substrates and products with a fluorescent tag using Huisgen 1,3-cycloaddition. FIGS. 7 and 8 illustrate the complete substrate profiles for wild-type *E. coli* GalK, the *E. coli* GalK mutant M173L, Y371H and M173L-Y371H.

To better understand the distinct role of the two particular amino acid residues (Met-173 and Tyr-371) in determining the substrate specificity, the inventor chose the native substrate D-galactose 29, the unique M173L substrate D-glucose 27 and the unique Y371H substrate L-altrose 41 for complete comparative steady-state kinetic profiling. In comparison to wild-type *E. coli* GalK, a slight (around 2-fold) D-galactose $K_m$ increase was observed in all three variants (M173L, Y371H and M173L-Y371H). Moreover, a comparison of the D-glucose kinetic parameters for M173L and the L-altrose kinetic values for Y371H to those of the double mutant revealed very little change. Thus, in contrast to the notable gain of function (in terms of the shear number of new M173L-Y371H substrates) illustrated in FIG. 7, the kinetic analysis only predicts the gain of function to be additive at best. In other words, the kinetic analysis predicts the double mutant should accept only known M173L and Y371H substrates but would not predict an expansion beyond this dual substrate set. Yet, while it is difficult to explain this remarkable gain of function in the M173L-Y371H variant, the unique ability of this double mutant to accept compounds 21, 22 and 46 sets the stage to assess the first step of in vivo glycorandomization as described below.

In Vivo Bioconversion of Unnatural Sugars Using an Engineered GalK. In the context of assessing in vivo bioconversion, the specific M173L-Y371H-22 relationship is advantageous for two reasons. First, as described above, 21, 22 and 46 are not a substrates for wild-type *E. coli* GalK and therefore, the use of a standard *E. coli* host strain (which contains the inherent wild-type *E. coli* GalK) should not interfere. Second, as previously mentioned, 21, 22 and 46 each offer a unique functional handle to provide for the rapid installation of a fluorescent label to simplify the chromatographic analysis. In this context, 22 and 46 are equally reactive to the required fluorescent-labeling via Husigen 1,3-cycloaddtion while 21 is poorly reactive (<10% X. Fu, unpublished). Thus, for the current in vivo analysis, 21 was excluded. The set selected (22 and 46) still offer the opportunity to test a range of substrates with distinctly unique in vitro profiles. Specifically, 22 is known to have >50% in vitro in 2 hrs while 46 shows ~15% conversion under the same conditions.

To assess the Y371H-M173L GalK-catalyzed in vivo production of unnatural sugar-1-phosphates (FIG. 9a), the unnatural sugars (22 or 46, 4 mM final concentration) were fed to an *E. coli* host (40 mL culture) which overexpressed the promiscuous GalK. After a designated time, the extracts were analyzed via the specific attachment of a fluorescent tag (50), to both starting material (22 or 46) and desired sugar-1-phosphate products, using 1,3-dipolar cycloaddition. Two controls were run in parallel. The first utilized a strain containing an empty expression vector (pET-15b—the vector used for overexpression of the GalK mutants) while the second employed a wild-type GalK overexpression strain. The crude products from each bioconversion were isolated, labelled via 1,3-dipolar cycloaddition and analyzed by fluorescence HPLC and LC-MS. As illustrated in FIG. 9b, ~69% conversion of 6-azido-6-deoxy-D-galactose (22) was observed, a slight improvement over the in vitro yield (~50% conversion). In a similar manner, ~15% conversion of 6-azido-6-deoxy-D-glucose (46) was observed, consistent with the in vitro yield (~50% conversion). Notably, this success illustrates that unnatural sugars are able to enter the heterologous *E. coli* host and access the engineered promiscuous sugar kinase. Given this key result, it is likely that the addition of a flexible nucleotidylytransferase (E2) and glycosyltransferase to this host will allow for in vivo glycorandomization.

Implications for In Vivo Glycorandomization

The recent developed chemoenzymatic approach in vitro glycorandomization significantly contributes to the diversity of novel therapeutics via altering glycosylation patterns on secondary metabolites. However, the general application of this approach is significantly limited by the two primary issues. First, expensive substrates/cofactors significantly hamper the scaling up the process, although the alternative solutions for regenerating these reagents are available. Second, the application of IVG to most, or all, classes of glycosylated natural products is heavily dependent upon the expression of appropriate glycosyltransferases and establishing in vitro conditions for an active enzyme which, in some cases, can be severely dictated by the solubility of the aglycon acceptor. The present advent of kinase-enhanced IVG potentially opens the door to in vivo applications of glycorandomization, and the inventor believes the in vivo process would be able to overcome these limitations. The current result illustrates the entry of unnatural sugars and their subsequent utilization by the engineered GalK. This result clearly stands as strong evidence supporting the overall feasibility of in vivo glycorandomization. As such, this work provides the foundation for the eventual glycorandomization a variety of clinically important secondary metabolites in vivo to rapidly enhance drug discovery efforts.

The sugar kinase with expanded substrate specificity useful for glycorandomization of the present invention has many other applications aside from those described in the preferred embodiment and examples. Thus, although the invention has been herein shown and described in what is perceived to be the most certain embodiments, it is to be understood that the invention is not intended to be limited to the specific embodiments set forth above. Rather, it is recognized that certain modifications, substitutions, alterations, omissions may be made by one of skill in the art of the invention without departing from the spirit or intent of the invention. Accordingly, the invention is to be taken as including all reasonable equivalents to the subject matter of the appended claims and the foregoing description is meant to be exemplary only and should not limit the scope of the invention set forth in the following claims.

All references are incorporated herein for all purposes.

REFERENCES (1) Weymouth-Wilson, A. C. (1997) *Nat. Prod. Rep.* 14, 99-110;

(2) Potier, P. (1999), *Actual Chim.* 11, 9-11.

(3) Thorson, J. S., & Vogt, T. in *Glycosylated Natural Products in Carbohydrate-based Drug Discovery,* 2003, ed: C.-W. Wong (Wiley-VCH Weinheim, Germany) Vol. II, pp 685-711.

(4) Kren, V., & Martinkova, L. (2001) *Curr. Med. Chem.* 8, 1303-1328.

(5) Kren, V. (2001) in *Glycoscience: Chemistry and Chemical Biology* I-III, eds: Fraser-Reid, B. O., Tatsuta, K., & Thiem, J. (Springer, Heidelberg, Germany), pp 2471-2529.

(6) Thorson, J. S., Hosted Jr., T. J., Jiang, J., Biggins, J. B., & Ahlert, J. (2001) *Curr. Org. Chem.* 5, 139-167.

(7) Albermann, C., Soriano, A., Jiang, J., Vollmer, H., Biggins, J. B., Barton, W. A., Lesniak, J., Nikolov, D. B., & Thorson, J. S. (2003) *Org. Lett.* 5, 933-936.

(8) Mendez, C. *Biotechnol.* 11, 449-456.

(9) Barton, W. A., Biggins, J. B., Jiang, J., Thorson, J. S., & Nikolov, D. B. (2002) *Proc. Natl. Acad. Sci. USA* 99, 13397-13402.

(10) Barton, W. A., Biggins, J. B., Lesniak, J., Jeffrey, P. D., Jiang, J., Rajashankar, K. R., Thorson, J. S., & Nikolov, D. B. (2001) *Nat. Struct. Biol.* 8, 545-551.

(11) Thorson, J. S., Barton, W. A., Hoffineister, D., Albermann, C., & Nikolov, D. B. (2003) *ChemBioChem,* 5:16-25.

(12) Jiang, J., Albermann, C., & Thorson, J. S. (2003) *ChemBioChem.* 4, 443-446;

(13) Fu, X., Albermann, C., Jiang, J., Liao, J., Zhang, C., & Thorson, J. S. (2003) Nat. Biotech. 21: 1467-1469.

(14) Jiang, J., Biggins, J. B., & Thorson, J. S. (2001) *Angew. Chem. Intl. Ed.* 40, 1502-1505.

(15) Jiang, J., Biggins, J. B., & Thorson, J. S. (2000) *J. Am. Chem. Soc.* 122, 6803-6804.

(16) Johnson, L. N., & Barford, D. (1990) *J. Biol. Chem.* 265, 2409-2412;

(17) Park, S. H., Pastuszak, I., Drake, R., & Elbein, A. D. (1998) *J. Biol. Chem.* 273, 5685-5691.

(18) Lavine, J. E., Cantlay, E., Roberts Jr., C. T., & Morse, D. E. (1982) *Biochim. Biophys. Acta* 717, 76-85.

(19) Dey, P. M. (1983) *Eur. J. Biochem.* 136, 155-159.

(20) Thomas, P., Bessell, E. M., & Westwood, J. H. (1974) *Biochem. J.* 139, 661-664.

(21) Yang, J., Fu, X., Jia, Q., Shen, J., Biggins, J. B., Jiang, J., Zhao, J., Schmidt, J. J., Wang, P. G. & Thorson, J. S. (2003) *Org. Lett.* 5, 2223-2226.

(22) Bornscheuer, U. T., & Pohl, M. (2001) *Curr. Opin. Chem. Biol.* 5, 137-143.

(23) Petrounia, I. P., & Arnold, F. H. (2000) *Curr. Opin. Biotechnol* 11, 325-330.

(24) Tao, H., & Cornish, V. W. (2002) *Curr. Opin. Chem. Biol.* 6, 858-864.

(25) Williams, G. J., Domann, S., Nelson, A., & Berry, A. (2003) *Proc. Natl. Acad. Sci. USA* 100, 3143-3148.

(26) Wada, M., Hsu, C. C., Franke, D., Mitchell, M., Heine, A., Wilson, I., & Wong, C.-H. (2003) *Bioorg. Med. Chem.* 11, 2091-2098.

(27) DeSantis, G., Liu, J., Clark, D. P., Heine, A., Wilson, I. A., & Wong, C.-H. (2003) *Bioorg. Med. Chem.* 11, 43-52.

(28) Leung, D. W., Chen, E., & Goeddel, D. V. (1989) *Technique* 1, 11-15.

(29) Cadwell, R. G, & Joyce, G. F. (1992) *PCR Meth. Appl* 2, 28-33.

(30) Liebeton, K., Zonta, A., Schimossek, K., Nardini, M., Lang, D., Dijkstra, B. W. Reetz, M. T. & Jaeger, K.-E. (2000) *Chem. Biol.* 7, 709-718.

(31) Stemmer, W. P. C. (1994) *Nature* 370, 389-391.

(32) Zhao, H., Giver, L., Shao, Z., Affholter, J. A. & Arnold, F. H. (1998) *Nat. Biotech.* 16, 258-261.

(33) Kikuchi, M., Ohnishi, K., & Harayama, S. (1999) *Gene* 236, 159-167.

(34) Coco, W. M., Levinson, W. E., Crist, M. J., Hektor, H. J., Darzins, A., Pienkos, P. T., Squires, C. H., & Monticello, D. J. (2001) *Nat. Biotech.* 19, 354-359.

(35) Miyazaki, K. (2002) *Nuc. Acids Res.* 30, e139.

(36) Zha, D., Eipper, A. & Reetz, M. T. (2003) *Chem Bio chem* 4, 34-39.

(37) Thoden, J. B. & Holden, H. M. (2003) *J. Biol. Chem.* 278 33305-33311.

(38) Debouck, C., Riccio, A., Schumperli, D., McKenney, K., Jeffers, J., Hughes, C., Rosenberg, M., Heuterspreute, M., Brunel, F., & Davison, J. (1985) *Nuc. Acids Res.* 13, 1841-1853.

(39) Blanc-Muesser, M., Defaye, J., Horton, D., & Tsai, J.-H. (1980) in *Methods in Carbohydrate Chemistry* Vol. VIII, eds: Whistler, R. L. & BeMiller, J. N. (Academic Press, Inc., New York), pp 177-183.

(40) Paulsen, H., Trautwein, W.-P., Espinosa, F. G., & Heyns, K. (1967) *Chem. Ber.* 100, 2822-2836.

(41) Paulsen, H., & Herold, C. P. (1970) *Chem. Ber.* 103, 2450-2462.

(42) Bradford, M. (1976) *Anal. Biochem.* 72, 248-254.

(43) Fromant, M., Blanquet, S., & Plateau, P. (1995) *Analyt. Biochem.* 224, 347-353.

(44) Bork, P., Sander, C., & Valencia, A. (1993) *Protein Sci.* 2, 31-40.

(45) Aleshin, A. E., Zeng, C., Bourenkov, G. P., Bartunik, H. D., Fromm, H. J., & Honzatko, R. B. (1998) *Structure* 6, 39-50.

(46) Segura, M. J. R., Lodeiro, S., Meyer, M. M., Patel, A. J., & Matsuda, S. P. (2002) *Org. Lett.* 4, 4459-4462.

(47) Joubert, B. M., Hua, L., & Matsuda, S. P. (2000) *Org. Lett.* 2, 339-341.

(48) Herrera, J. B., Wilson, W. K., & Matsuda, S. P. (2000) *J. Am. Chem. Soc.* 122, 6765-6766.

(49) Segura, M. J., Jackson, B. E., & Matsuda, S. P. (2003) *Nat. Prod. Rep.* 20, 304-317.

(50) Otten, L. G., Sio, C. F., Vrielink, J., Cool, R. H., & Quax, W. J. (2002) *J. Biol. Chem.* 277, 42121-42127.

(51) Hoffineister, D., Yang, J., Liu, L., Thorson, J. S. (2003) *Proc. Natl. Acad. Sci. USA* 100, 13184-13189.

(52) Hoffineister, D., Thorson, J. S. (2004) *ChemBioChem* 5, 989-992.

(53) Yang, J.; Liu, L.; Thorson, J. S. (2004) *ChemBioChem* 5, 992-996.

(54) Northrup, A. B., MacMillan, D. W. (2004) *Science.* 305, 1752-1755.

(55) Northrup A. B., Mangion, I. K., Hettche, F., MacMillan, D. W. (2004) *Angew Chem Int Ed Engl.* 43, 2152-2154.

(56) Yang, J., Hoffineister, D., Liu, L., Fu, X., Thorson, J. S. (2004) *Bioorg. Med. Chem.* 12, 1577-1584.

(57) Langenhan, J. M., Thorson, J. S. (2004) *Curr. Org. Syn.* manuscript in press.

(58) Zhang, J., Kowal, P., Chen, X., Wang, P. G. (2003) *Org. Biomol. Chem.* 1, 3048-3053.

(59) Zhang, J., Chen, X., Shao, J., Liu, Z., Kowal, P., Lu, Y., Wang, P. G. (2003) *Methods Enzymol.* 362,106-124.

(60) Luchansky, S. J., Hang, H. C., Saxon, E., Grunwell, J. R., Yu, C., Dube, D. H., Bertozzi, C. R. (2003) *Methods Enzymol.* 362, 249-272.

(61) Fuster, M. M., Brown, J. R., Wang, L., Esko, J. D. (2003) *Cancer Res.* 63, 2775-2781.

(62) Mong, T. K., Lee, L. V., Brown, J. R., Esko, J. D., Wong, C. H. (2003) *Chembiochem.* 4, 835-840.

(63) Shao, J., Hayashi T., Wang P. G. (2003) *Appl. Environ. Microbiol* 69, 5238-5342.

(64) Thoden, J. B., & Holden, H. M. (2003) *J. Biol. Chem.* 278, 33305-33311.

(65) Bradford, M. (1976) *Anal. Biochem.* 72, 248-254.

What is claimed is:

1. An isolated galactokinase (GalK) variant having the amino acid sequence set forth in SEQ ID NO: 1, wherein tyrosine 371 is mutated to histidine (Y371H) and methionine 173 is mutated to leucine (M173L), wherein the GalK variant has expanded sugar substrate specificity, as compared to the non-mutated GalK set forth in SEQ ID NO: 1.

2. The isolated GalK variant of claim 1, wherein said variant displays substrate specificity toward a D or L sugar.

3. The isolated GalK variant of claim 2, wherein the D or L sugar is selected from the group consisting of D-glactose, 2-deoxyD-galactose, D-galactose-amine, D-talose, 3-deoxy-D-galactose, 6-deoxy -D-galactose, 6-amino-D-galactose, D-galacturonic acid,L-altrose and L-glucose.

4. An isolated GalK variant having the amino acid sequence set forth in SEQ ID NO: 1, wherein tyrosine 371 is mutated to histidine (Y371 H) and methionine 173 is mutated to leucine (M173L).

5. The GalK variant of claim 4, wherein said variant displays catalytic activity toward a D or L sugar selected from the group consisting of D-galactose, 2-deoxy D-galactose, D-galactose-amine, D-talose, 3-deoxy- D-galactose, 6-deoxy- D-galactose, 6amino- D-galactose, D-galacturonic acid, L-altrose and L-glucose.

* * * * *

SEQUENCE LISTING

<160> NUMBER OF SEQ ID NOS: 14

<210> SEQ ID NO 1
<211> LENGTH: 382
<212> TYPE: PRT
<213> ORGANISM: Escherichia coli

<400> SEQUENCE: 1

```
Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
    50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
    130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
    210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ala Ser Ala Leu Glu Gln Gly Asp Leu Lys
        275                 280                 285

Arg Met Gly Glu Leu Met Ala Glu Ser His Ala Ser Met Arg Asp Asp
    290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Gly Phe
                325                 330                 335

Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
```

```
                355                 360                 365
Thr Phe Tyr Val Cys Lys Pro Ser Gln Gly Ala Gly Gln Cys
        370                 375                 380

<210> SEQ ID NO 2
<211> LENGTH: 382
<212> TYPE: PRT
<213> ORGANISM: Escherichia coli
<220> FEATURE:
<221> NAME/KEY: misc_feature
<222> LOCATION: (28)..(28)
<223> OTHER INFORMATION: Xaa can be any naturally occurring amino acid

<400> SEQUENCE: 2

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Xaa Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ser Ala Leu Glu Gln Gly Asp Leu Lys
        275                 280                 285

Arg Met Gly Glu Leu Met Ala Glu Ser His Ala Ser Met Arg Asp Asp
290                 295                 300

Phe Glu Ile Thr Val Pro Gln Ile Asp Thr Leu Val Glu Ile Val Lys
305                 310                 315                 320

Ala Val Ile Gly Asp Lys Gly Gly Val Arg Met Thr Gly Gly Gly Phe
                325                 330                 335
```

```
Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
        355                 360                 365

Thr Phe Tyr Val Cys Lys Pro Ser Gln Gly Ala Gly Gln Cys
    370                 375                 380

<210> SEQ ID NO 3
<211> LENGTH: 382
<212> TYPE: PRT
<213> ORGANISM: Escherichia coli
<220> FEATURE:
<221> NAME/KEY: misc_feature
<222> LOCATION: (34)..(34)
<223> OTHER INFORMATION: Xaa can be any naturally occurring amino acid

<400> SEQUENCE: 3

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Xaa His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
    130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
    210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ala Ser Ala Leu Glu Gln Gly Asp Leu Lys
        275                 280                 285

Arg Met Gly Glu Leu Met Ala Glu Ser His Ala Ser Met Arg Asp Asp
    290                 295                 300
```

-continued

```
Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Gly Phe
            325                 330                 335

Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
        355                 360                 365

Thr Phe Tyr Val Cys Lys Pro Ser Gln Gly Ala Gly Gln Cys
370                 375                 380

<210> SEQ ID NO 4
<211> LENGTH: 382
<212> TYPE: PRT
<213> ORGANISM: Escherichia coli
<220> FEATURE:
<221> NAME/KEY: misc_feature
<222> LOCATION: (37)..(37)
<223> OTHER INFORMATION: Xaa can be any naturally occurring amino acid

<400> SEQUENCE: 4

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Xaa Tyr Asn Asp Gly Phe Val Leu Pro Cys Ala Ile
            35                  40                  45

Asp Tyr Gln Thr Val Ile Ser Cys Ala Pro Arg Asp Asp Arg Lys Val
50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
            115                 120                 125

Ser Ser Ala Ser Leu Glu Val Ala Val Gly Thr Val Leu Gln Gln Leu
        130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ala Ser Ala Leu Glu Gln Gly Asp Leu Lys
```

```
                  275                 280                 285
Arg Met Gly Glu Leu Met Ala Glu Ser His Ala Ser Met Arg Asp Asp
            290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Gly Gly Phe
                325                 330                 335

Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
            355                 360                 365

Thr Phe Tyr Val Cys Lys Pro Ser Gln Gly Ala Gly Gln Cys
370                 375                 380

<210> SEQ ID NO 5
<211> LENGTH: 382
<212> TYPE: PRT
<213> ORGANISM: Escherichia coli
<220> FEATURE:
<221> NAME/KEY: misc_feature
<222> LOCATION: (174)..(174)
<223> OTHER INFORMATION: Xaa can be any naturally occurring amino acid

<400> SEQUENCE: 5

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
                20                  25                  30

Gly Glu His Thr Asp Tyr Asn Asp Gly Phe Val Leu Pro Cys Ala Ile
            35                  40                  45

Asp Tyr Gln Thr Val Ile Ser Cys Ala Pro Arg Asp Asp Arg Lys Val
        50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Xaa Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
    210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255
```

```
Leu Asp Pro Ile Val Ala Lys Arg Val Arg His Ile Leu Thr Glu Asn
        260                 265                 270

Ala Arg Thr Val Glu Ala Ala Ser Ala Leu Glu Gln Gly Asp Leu Lys
        275                 280                 285

Arg Met Gly Glu Leu Met Ala Glu Ser His Ala Ser Met Arg Asp Asp
        290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Phe
                325                 330                 335

Gly Gly Cys Ile Val Ala Leu Ile Pro Glu Glu Leu Val Pro Ala Val
        340                 345                 350

Gln Gln Ala Val Ala Glu Gln Tyr Glu Ala Lys Thr Gly Ile Lys Glu
        355                 360                 365

Thr Phe Tyr Val Cys Lys Pro Ser Gln Gly Ala Gly Gln Cys
        370                 375                 380

<210> SEQ ID NO 6
<211> LENGTH: 399
<212> TYPE: PRT
<213> ORGANISM: Lactococcus lactis
<220> FEATURE:
<221> NAME/KEY: misc_feature
<222> LOCATION: (233)..(233)
<223> OTHER INFORMATION: Xaa can be any naturally occurring amino acid

<400> SEQUENCE: 6

Met Ser Ile Val Val Glu Asn Ser Thr Val Leu Ser Ala Leu Thr Glu
1               5                   10                  15

Lys Phe Ala Glu Val Phe Gly Asp Thr Lys Glu Val Glu Tyr Phe Phe
            20                  25                  30

Ser Pro Gly Arg Ile Asn Leu Ile Gly Glu His Thr Asp Tyr Asn Gly
        35                  40                  45

Gly Tyr Val Phe Pro Ala Ser Ile Ile Gly Thr Thr Gly Leu Ala
    50                  55                  60

Arg Leu Arg Glu Asp Lys Lys Val Lys Leu Tyr Ser Glu Asn Phe Pro
65              70                  75                  80

Lys Leu Gly Val Ile Glu Phe Asp Leu Asp Glu Val Glu Lys Lys Asp
                85                  90                  95

Gly Glu Leu Trp Ser Asn Tyr Val Lys Gly Met Ile Val Met Leu Lys
            100                 105                 110

Gly Ala Gly Tyr Glu Ile Asp Lys Gly Phe Glu Leu Leu Ile Lys Gly
        115                 120                 125

Glu Ile Pro Thr Ala Ser Gly Leu Ser Ser Ser Ala Ser Leu Glu Leu
    130                 135                 140

Leu Val Gly Val Val Leu Asp Asp Leu Phe Asn Leu Asn Val Pro Arg
145                 150                 155                 160

Leu Glu Leu Val Gln Leu Gly Gln Lys Thr Glu Asn Asp Tyr Ile Gly
                165                 170                 175

Val Asn Ser Gly Ile Leu Asp Gln Phe Ala Ile Gly Phe Gly Glu Val
            180                 185                 190

Lys Lys Ala Ile Leu Leu Asp Cys Asn Thr Leu Lys Tyr Glu Met Val
        195                 200                 205

Pro Val Glu Leu Arg Asp Tyr Asp Ile Val Ile Met Asn Thr Asn Lys
    210                 215                 220
```

```
Pro Arg Ala Leu Thr Glu Ser Lys Xaa Asn Glu Arg Phe Ala Glu Thr
225                 230                 235                 240

Arg Glu Ala Leu Lys Arg Met Gln Thr Arg Leu Asp Ile Gln Ser Leu
            245                 250                 255

Gly Glu Leu Ser Asn Glu Glu Phe Asp Ala Asn Thr Asp Leu Ile Gly
        260                 265                 270

Asp Glu Thr Leu Ile Lys Arg Ala Arg His Ala Val Tyr Glu Asn Asn
    275                 280                 285

Arg Thr Lys Ile Ala Gln Lys Ala Phe Val Ala Gly Asn Leu Thr Lys
290                 295                 300

Phe Gly Glu Leu Leu Asn Ala Ser His Ala Ser Leu Lys Asp Asp Tyr
305                 310                 315                 320

Glu Val Thr Gly Leu Glu Leu Asp Thr Leu Ala Glu Thr Ala Gln Lys
            325                 330                 335

Gln Ala Gly Val Leu Gly Ala Arg Met Thr Gly Ala Gly Phe Gly Gly
        340                 345                 350

Cys Ala Ile Ala Leu Val Ala His Asp Asn Val Ser Ala Phe Glu Lys
    355                 360                 365

Ala Val Gly Gln Val Tyr Glu Glu Val Val Gly Tyr Pro Ala Ser Phe
370                 375                 380

Tyr Val Ala Gln Ile Gly Ser Gly Ser Thr Lys Leu Asp Val Glu
385                 390                 395

<210> SEQ ID NO 7
<211> LENGTH: 382
<212> TYPE: PRT
<213> ORGANISM: Escherichia coli
<220> FEATURE:
<221> NAME/KEY: misc_feature
<222> LOCATION: (339)..(339)
<223> OTHER INFORMATION: Xaa can be any naturally occurring amino acid

<400> SEQUENCE: 7

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
    50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
            85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
    130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
            165                 170                 175

Ile Ser Ala Leu Gly Lys Lys Asp His Ala Leu Leu Ile Asp Cys Arg
```

```
                    180                 185                 190
Ser Leu Gly Thr Lys Ala Val Ser Met Pro Lys Gly Val Ala Val Val
            195                 200                 205

Ile Ile Asn Ser Asn Phe Lys Arg Thr Leu Val Gly Ser Glu Tyr Asn
        210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ser Ala Leu Glu Gln Gly Asp Leu Lys
        275                 280                 285

Arg Met Gly Glu Leu Met Ala Glu Ser His Ala Ser Met Arg Asp Asp
290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Phe
                325                 330                 335

Gly Gly Xaa Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
        355                 360                 365

Thr Phe Tyr Val Cys Lys Pro Ser Gln Gly Ala Gly Gln Cys
370                 375                 380

<210> SEQ ID NO 8
<211> LENGTH: 382
<212> TYPE: PRT
<213> ORGANISM: Escherichia coli

<400> SEQUENCE: 8

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
    50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
    130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
                165                 170                 175
```

```
Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
            195                 200                 205

Ile Ile Asn Ser Asn Phe Lys Arg Thr Leu Val Gly Ser Glu Tyr Asn
            210                 215                 220

Thr Arg Arg Glu Gln Cys Glu Thr Gly Ala Arg Phe Phe Gln Pro
225                 230                 235                 240

Ala Leu Arg Asp Val Thr Ile Glu Glu Phe Asn Ala Val Ala His Glu
            245                 250                 255

Leu Asp Pro Ile Val Ala Lys Arg Val Arg His Ile Leu Thr Glu Asn
            260                 265                 270

Ala Arg Thr Val Glu Ala Ser Ala Leu Glu Gln Gly Asp Leu Lys
            275                 280                 285

Arg Met Gly Glu Leu Met Ala Glu Ser His Ala Ser Met Arg Asp Asp
    290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Phe
            325                 330                 335

Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
            355                 360                 365

Thr Phe His Val Cys Lys Pro Ser Gln Gly Ala Gly Gln Cys
    370                 375                 380

<210> SEQ ID NO 9
<211> LENGTH: 382
<212> TYPE: PRT
<213> ORGANISM: Escherichia coli
<220> FEATURE:
<221> NAME/KEY: misc_feature
<222> LOCATION: (371)..(371)
<223> OTHER INFORMATION: Xaa can be any naturally occurring amino acid

<400> SEQUENCE: 9

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
    50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
            85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
    130                 135                 140

Tyr His Leu Pro Leu Asp Gly Ala Gln Ile Ala Leu Asn Gly Gln Glu
```

```
                145                 150                 155                 160
Ala Glu Asn Gln Phe Val Gly Cys Asn Cys Gly Ile Met Asp Gln Leu
                165                 170                 175

Ile Ser Ala Leu Gly Lys Lys Asp His Ala Leu Leu Ile Asp Cys Arg
                180                 185                 190

Ser Leu Gly Thr Lys Ala Val Ser Met Pro Lys Gly Val Ala Val Val
                195                 200                 205

Ile Ile Asn Ser Asn Phe Lys Arg Thr Leu Val Gly Ser Glu Tyr Asn
            210                 215                 220

Thr Arg Arg Glu Gln Cys Glu Thr Gly Ala Arg Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
                260                 265                 270

Ala Arg Thr Val Glu Ala Ala Ser Ala Leu Glu Gln Gly Asp Leu Lys
                275                 280                 285

Arg Met Gly Glu Leu Met Ala Glu Ser His Ala Ser Met Arg Asp Asp
290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Phe
                325                 330                 335

Gly Gly Cys Ile Val Ala Leu Ile Pro Glu Glu Leu Val Pro Ala Val
                340                 345                 350

Gln Gln Ala Val Ala Glu Gln Tyr Glu Ala Lys Thr Gly Ile Lys Glu
                355                 360                 365

Thr Phe Xaa Val Cys Lys Pro Ser Gln Gly Ala Gly Gln Cys
                370                 375                 380

<210> SEQ ID NO 10
<211> LENGTH: 382
<212> TYPE: PRT
<213> ORGANISM: Escherichia coli

<400> SEQUENCE: 10

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
                20                  25                  30

Gly Glu His Thr Asp Tyr Asn Asp Gly Phe Val Leu Pro Cys Ala Ile
            35                  40                  45

Asp Tyr Gln Thr Val Ile Ser Cys Ala Pro Arg Asp Asp Arg Lys Val
        50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
                100                 105                 110

Val Asp Met Val Ile Ser Gly Asn Val Pro Gln Gly Ala Gly Leu Ser
            115                 120                 125

Ser Ser Ala Ser Leu Glu Val Ala Val Gly Thr Val Leu Gln Gln Leu
        130                 135                 140
```

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Leu Asp Gln Leu
            165                 170                 175

Ile Ser Ala Leu Gly Lys Lys Asp His Ala Leu Leu Ile Asp Cys Arg
        180                 185                 190

Ser Leu Gly Thr Lys Ala Val Ser Met Pro Lys Gly Val Ala Val Val
    195                 200                 205

Ile Ile Asn Ser Asn Phe Lys Arg Thr Leu Val Gly Ser Glu Tyr Asn
210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
            245                 250                 255

Leu Asp Pro Ile Val Ala Lys Arg Val Arg His Ile Leu Thr Glu Asn
        260                 265                 270

Ala Arg Thr Val Glu Ala Ala Ser Ala Leu Glu Gln Gly Asp Leu Lys
    275                 280                 285

Arg Met Gly Glu Leu Met Ala Glu Ser His Ala Ser Met Arg Asp Asp
290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Phe
            325                 330                 335

Gly Gly Cys Ile Val Ala Leu Ile Pro Glu Glu Leu Val Pro Ala Val
        340                 345                 350

Gln Gln Ala Val Ala Glu Gln Tyr Glu Ala Lys Thr Gly Ile Lys Glu
    355                 360                 365

Thr Phe Tyr Val Cys Lys Pro Ser Gln Gly Ala Gly Gln Cys
370                 375                 380

<210> SEQ ID NO 11
<211> LENGTH: 382
<212> TYPE: PRT
<213> ORGANISM: Escherichia coli
<220> FEATURE:
<221> NAME/KEY: misc_feature
<222> LOCATION: (173)..(173)
<223> OTHER INFORMATION: Xaa can be any naturally occurring amino acid

<400> SEQUENCE: 11

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
    50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
            85                  90                  95

Arg Gly Val Val Lys His Leu Gln Leu Arg Asn Asn Ser Phe Gly Gly
        100                 105                 110

Val Asp Met Val Ile Ser Gly Asn Val Pro Gln Gly Ala Gly Leu Ser

```
            115                 120                 125
Ser Ser Ala Ser Leu Glu Val Ala Val Gly Thr Val Leu Gln Gln Leu
        130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Xaa Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
    210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ala Ser Ala Leu Glu Gln Gly Asp Leu Lys
        275                 280                 285

Arg Met Gly Glu Leu Met Ala Glu Ser His Ala Ser Met Arg Asp Asp
    290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Gly Phe
                325                 330                 335

Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
        355                 360                 365

Thr Phe Tyr Val Cys Lys Pro Ser Gln Gly Ala Gly Gln Cys
    370                 375                 380

<210> SEQ ID NO 12
<211> LENGTH: 382
<212> TYPE: PRT
<213> ORGANISM: Escherichia coli

<400> SEQUENCE: 12

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
                20                  25                  30

Gly Glu His Thr Asp Tyr Asn Asp Gly Phe Val Leu Pro Cys Ala Ile
            35                  40                  45

Asp Tyr Gln Thr Val Ile Ser Cys Ala Pro Arg Asp Asp Arg Lys Val
        50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110
```

Val Asp Met Val Ile Ser Gly Asn Val Pro Gln Gly Ala Gly Leu Ser
            115                 120                 125

Ser Ser Ala Ser Leu Glu Val Ala Val Gly Thr Val Leu Gln Gln Leu
        130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Leu Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ala Ser Ala Leu Glu Gln Gly Asp Leu Lys
        275                 280                 285

Arg Met Gly Glu Leu Met Ala Glu Ser His Ala Ser Met Arg Asp Asp
290                 295                 300

Phe Glu Ile Thr Val Pro Gln Ile Asp Thr Leu Val Glu Ile Val Lys
305                 310                 315                 320

Ala Val Ile Gly Asp Lys Gly Val Arg Met Thr Gly Gly Phe
                325                 330                 335

Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
        355                 360                 365

Thr Phe His Val Cys Lys Pro Ser Gln Gly Ala Gly Gln Cys
370                 375                 380

<210> SEQ ID NO 13
<211> LENGTH: 399
<212> TYPE: PRT
<213> ORGANISM: Lactococcus lactis
<220> FEATURE:
<221> NAME/KEY: misc_feature
<222> LOCATION: (353)..(353)
<223> OTHER INFORMATION: Xaa can be any naturally occurring amino acid

<400> SEQUENCE: 13

Met Ser Ile Val Val Glu Asn Ser Thr Val Leu Ser Ala Leu Thr Glu
1               5                   10                  15

Lys Phe Ala Glu Val Phe Gly Asp Thr Lys Glu Val Glu Tyr Phe Phe
                20                  25                  30

Ser Pro Gly Arg Ile Asn Leu Ile Gly Glu His Thr Asp Tyr Asn Gly
            35                  40                  45

Gly Tyr Val Phe Pro Ala Ser Ile Ile Gly Thr Thr Gly Leu Ala
        50                  55                  60

Arg Leu Arg Glu Asp Lys Lys Val Lys Leu Tyr Ser Glu Asn Phe Pro
65                  70                  75                  80

Lys Leu Gly Val Ile Glu Phe Asp Leu Asp Glu Val Glu Lys Lys Asp

-continued

```
                 85                  90                  95
Gly Glu Leu Trp Ser Asn Tyr Val Lys Gly Met Ile Val Met Leu Lys
            100                 105                 110
Gly Ala Gly Tyr Glu Ile Asp Lys Gly Phe Glu Leu Leu Ile Lys Gly
            115                 120                 125
Glu Ile Pro Thr Ala Ser Gly Leu Ser Ser Ala Ser Leu Glu Leu
            130                 135                 140
Leu Val Gly Val Val Leu Asp Asp Leu Phe Asn Leu Asn Val Pro Arg
145                 150                 155                 160
Leu Glu Leu Val Gln Leu Gly Gln Lys Thr Glu Asn Asp Tyr Ile Gly
                165                 170                 175
Val Asn Ser Gly Ile Leu Asp Gln Phe Ala Ile Gly Phe Gly Glu Val
            180                 185                 190
Lys Lys Ala Ile Leu Leu Asp Cys Asn Thr Leu Lys Tyr Glu Met Val
            195                 200                 205
Pro Val Glu Leu Arg Asp Tyr Asp Ile Val Ile Met Asn Thr Asn Lys
            210                 215                 220
Pro Arg Ala Leu Thr Glu Ser Lys Tyr Asn Glu Arg Phe Ala Glu Thr
225                 230                 235                 240
Arg Glu Ala Leu Lys Arg Met Gln Thr Arg Leu Asp Ile Gln Ser Leu
                245                 250                 255
Gly Glu Leu Ser Asn Glu Glu Phe Asp Ala Asn Thr Asp Leu Ile Gly
            260                 265                 270
Asp Glu Thr Leu Ile Lys Arg Ala Arg His Ala Val Tyr Glu Asn Asn
            275                 280                 285
Arg Thr Lys Ile Ala Gln Lys Ala Phe Val Ala Gly Asn Leu Thr Lys
            290                 295                 300
Phe Gly Glu Leu Leu Asn Ala Ser His Ala Ser Leu Lys Asp Asp Tyr
305                 310                 315                 320
Glu Val Thr Gly Leu Glu Leu Asp Thr Leu Ala Glu Thr Ala Gln Lys
                325                 330                 335
Gln Ala Gly Val Leu Gly Ala Arg Met Thr Gly Ala Gly Phe Gly Gly
            340                 345                 350
Xaa Ala Ile Ala Leu Val Ala His Asp Asn Val Ser Ala Phe Glu Lys
            355                 360                 365
Ala Val Gly Gln Val Tyr Glu Glu Val Val Gly Tyr Pro Ala Ser Phe
            370                 375                 380
Tyr Val Ala Gln Ile Gly Ser Gly Ser Thr Lys Leu Asp Val Glu
385                 390                 395

<210> SEQ ID NO 14
<211> LENGTH: 399
<212> TYPE: PRT
<213> ORGANISM: Lactococcus lactis

<400> SEQUENCE: 14

Met Ser Ile Val Val Glu Asn Ser Thr Val Leu Ser Ala Leu Thr Glu
1               5                   10                  15
Lys Phe Ala Glu Val Phe Gly Asp Thr Lys Glu Val Glu Tyr Phe Phe
                20                  25                  30
Ser Pro Gly Arg Ile Asn Leu Ile Gly Glu His Thr Asp Tyr Asn Gly
            35                  40                  45
```

-continued

```
Gly Tyr Val Phe Pro Ala Ser Ile Ile Ile Gly Thr Thr Gly Leu Ala
    50                  55                  60

Arg Leu Arg Glu Asp Lys Lys Val Lys Leu Tyr Ser Glu Asn Phe Pro
65              70                  75                  80

Lys Leu Gly Val Ile Glu Phe Asp Leu Asp Glu Val Glu Lys Lys Asp
                85                  90                  95

Gly Glu Leu Trp Ser Asn Tyr Val Lys Gly Met Ile Val Met Leu Lys
            100                 105                 110

Gly Ala Gly Tyr Glu Ile Asp Lys Gly Phe Glu Leu Leu Ile Lys Gly
        115                 120                 125

Glu Ile Pro Thr Ala Ser Gly Leu Ser Ser Ser Ala Ser Leu Glu Leu
    130                 135                 140

Leu Val Gly Val Val Leu Asp Asp Leu Phe Asn Leu Asn Val Pro Arg
145                 150                 155                 160

Leu Glu Leu Val Gln Leu Gly Gln Lys Thr Glu Asn Asp Tyr Ile Gly
                165                 170                 175

Val Asn Ser Gly Ile Leu Asp Gln Phe Ala Ile Gly Phe Gly Glu Val
            180                 185                 190

Lys Lys Ala Ile Leu Leu Asp Cys Asn Thr Leu Lys Tyr Glu Met Val
        195                 200                 205

Pro Val Glu Leu Arg Asp Tyr Asp Ile Val Ile Met Asn Thr Asn Lys
    210                 215                 220

Pro Arg Ala Leu Thr Glu Ser Lys Tyr Asn Glu Arg Phe Ala Glu Thr
225                 230                 235                 240

Arg Glu Ala Leu Lys Arg Met Gln Thr Arg Leu Asp Ile Gln Ser Leu
                245                 250                 255

Gly Glu Leu Ser Asn Glu Glu Phe Asp Ala Asn Thr Asp Leu Ile Gly
            260                 265                 270

Asp Glu Thr Leu Ile Lys Arg Ala Arg His Ala Val Tyr Glu Asn Asn
        275                 280                 285

Arg Thr Lys Ile Ala Gln Lys Ala Phe Val Ala Gly Asn Leu Thr Lys
    290                 295                 300

Phe Gly Glu Leu Leu Asn Ala Ser His Ala Ser Leu Lys Asp Asp Tyr
305                 310                 315                 320

Glu Val Thr Gly Leu Glu Leu Asp Thr Leu Ala Glu Thr Ala Gln Lys
                325                 330                 335

Gln Ala Gly Val Leu Gly Ala Arg Met Thr Gly Ala Gly Phe Gly Gly
            340                 345                 350

Cys Ala Ile Ala Leu Val Ala His Asp Asn Val Ser Ala Phe Glu Lys
        355                 360                 365

Ala Val Gly Gln Val Tyr Glu Glu Val Val Gly Tyr Pro Ala Ser Phe
    370                 375                 380

Tyr Val Ala Gln Ile Gly Ser Gly Ser Thr Lys Leu Asp Val Glu
385                 390                 395
```